(12) United States Patent
Evans et al.

(10) Patent No.: US 9,217,812 B2
(45) Date of Patent: Dec. 22, 2015

(54) PHOTOCHROMIC POLYMER

(75) Inventors: Richard Alexander Evans, Glen Waverley (AU); Nino Malic, Ferntree Gully (AU)

(73) Assignee: Vivimed Labs Europe LTD, Huddersfield (GB)

( * ) Notice: Subject to any disclaimer, the term of this patent is extended or adjusted under 35 U.S.C. 154(b) by 59 days.

(21) Appl. No.: 14/112,210

(22) PCT Filed: May 2, 2012

(86) PCT No.: PCT/AU2012/000458
§ 371 (c)(1),
(2), (4) Date: Oct. 16, 2013

(87) PCT Pub. No.: WO2012/149599
PCT Pub. Date: Nov. 8, 2012

(65) Prior Publication Data
US 2014/0042377 A1    Feb. 13, 2014

Related U.S. Application Data

(60) Provisional application No. 61/481,830, filed on May 3, 2011.

(51) Int. Cl.
| | |
|---|---|
| *G02B 1/04* | (2006.01) |
| *C07D 311/92* | (2006.01) |
| *C07D 498/10* | (2006.01) |
| *C09K 9/02* | (2006.01) |
| *C08G 65/331* | (2006.01) |
| *C08G 65/332* | (2006.01) |
| *C08G 65/333* | (2006.01) |
| *G02B 5/23* | (2006.01) |

(52) U.S. Cl.
CPC .............. *G02B 1/041* (2013.01); *C07D 311/92* (2013.01); *C07D 498/10* (2013.01); *C08G 65/3315* (2013.01); *C08G 65/3324* (2013.01); *C08G 65/33396* (2013.01); *C09K 9/02* (2013.01); *G02B 1/04* (2013.01); *G02B 1/043* (2013.01); *C09K 2211/145* (2013.01); *C09K 2211/1416* (2013.01); *C09K 2211/1425* (2013.01); *C09K 2211/1433* (2013.01); *C09K 2211/1466* (2013.01); *C09K 2211/1475* (2013.01); *G02B 5/23* (2013.01)

(58) Field of Classification Search
CPC ........ C08G 65/02; C08G 65/04; C08G 65/06; C08G 65/2615; C08G 65/2609; C08G 65/33396; C08G 65/3324; C08G 65/3315; G02B 1/00; G02B 1/04; G02B 1/041; G02B 1/043
See application file for complete search history.

(56) References Cited

U.S. PATENT DOCUMENTS 3,530,075 A    9/1970    Wiebe

FOREIGN PATENT DOCUMENTS

WO    2009146509 A1    12/2009

OTHER PUBLICATIONS

Liu et al., "Approach to Peptide Decorated Micelles via RAFT Polymerization," Journal of Polymer Science 47:899-912 (2009).
Eckert et al., "Photophysics of Adsorbed and Solution Phase End-Tagged Poly(ethylene oxide)," J. Phys. Chem. 98:12025-12031 (1994).
Hsiao et al., "Excited-State Electron Transfer from Anthracene and Pyrene Covalently End-Tagged onto Poly (ethylene oxide)," J. Phys. Chem. 98:12032-12039 (1994).
PCT International Search Report for PCT/AU2012000458, filed May 2, 2012 (mailed Jul. 20, 2012).

*Primary Examiner* — Michael L Leonard
(74) *Attorney, Agent, or Firm* — LeClairRyan, a Professional Corporation

(57) ABSTRACT

A photochromic polymer comprising at least two photochromic moieties linked by a straight or branched chain polymer selected from the group consisting of poly($C_2$ to $C_4$ alkylene oxide), poly[$C_1$ to $C_{10}$ alkoxy substituted ($C_2$ to $C_4$ alkylene oxide)] and poly[$C_1$ to $C_{-15}$ acyloxy substituted ($C_2$ to $C_4$ alkylene oxide)].

18 Claims, 3 Drawing Sheets

PHOTOCHROMIC POLYMER

This Patent Application claims priority from U.S. Provisional Patent Application No. 61/481,830, filed 3 May 2011, the contents of which are herein incorporated by reference.

FIELD

The invention relates to a photochromic polymer and in particular to a linear or branched poly(alkylene oxide) polymer linking at least two photochromic moieties and to polymeric compositions comprising a host polymer and the photochromic polymer and to methods of preparing the photochromic polymer and polymeric compositions comprising the photochromic polymer.

BACKGROUND

Photochromism is a property which has been used in the manufacture of light transmissible articles for many years. A compound is said to be photochromic if it changes colour when irradiated and reverts to its original colour when irradiation ceases. The use of photochromics in the manufacture of spectacle lenses is a particular benefit as it enables the efficiency with which radiation is filtered to be varied with the intensity of radiation. Photochromics also have potential for use in a range of other polymeric compositions in products or in applications such as architectural, automotive and aircraft windows and transparencies; inks, paints and coating compositions; optical sensors, filters, switches and data storage devices; and for security and UV exposure sensing applications.

Despite the successful use of photochromic compounds in applications such as lenses there remain limitations which reduce the versatility and potential of this technology. It is advantageous to control the rate at which photochromic polymeric compositions transform to their coloured state when exposed to radiation and fade to clear on cessation of this exposure. In many situations, it is important to provide rapid colouring and fading kinetics particularly for lenses and spectacles. In the past a compromise had to be made in the components and properties of the substrate to enhance the rate of coloration and fade. For example, many photochromics colour and fade more rapidly in soft materials and yet, for applications such as spectacles, abrasion resistance and hardness are important. This trade off between rate of transformation and hardness produces a dilemma for manufacturers between toughness and photochromic efficiency. In polymeric lenses many photochromics exhibit a slower rate of fade than is desirable.

International Application WO2004/041961 describes photochromic adducts which comprise a photochromic moiety and one or more polyether or siloxane oligomers. The presence of the oligomers can significantly improve the rate of coloration and fade particularly in the case of polydialkylsiloxane oligomers. International patent application WO 2009/146509 discloses a photochromic polymers which include two or more photochromic moieties linked via a polydialkylsiloxane chain. The polydialkylsiloxane adducts containing a single photochromic show a propensity to phase separate with increased loading in host polymers used for lens materials. Phase separation is reduced for siloxanes substituted with two or more photochromic moieties but we have found that the propensity for phase separation is may still be a problem at high loadings. Another problem we have found with siloxane photochromic polymers is their susceptibility to acid degradation which requires special synthetic approaches which are less attractive for industrial manufacture.

SUMMARY

We have now found that the fade speed of photochromic polymers comprising two or more photochromic moieties linked by certain polyalkylene oxide polymers have photochromic performance comparable to the siloxanes and improved compatibility, stability and ease of synthesis.

We provide a photochromic polymer comprising at least two photochromic moieties linked by a straight or branched chain polymer selected from the group consisting of poly($C_2$ to $C_4$ alkylene oxide), poly[$C_1$ to $C_{10}$ alkoxy substituted ($C_2$ to $C_4$ alkylene oxide)] and poly[$C_1$ to $C_{15}$ acyloxy substituted ($C_2$ to $C_4$ alkylene oxide)].

Generally the photochromic polymer will not comprise silicon such as poly(dialkylsiloxane).

The molecular weight of the polyalkylene oxide is not narrowly critical but is typically in the range of from 200 to 10000 and more preferably from 400 to 5000.

In one set of embodiments the invention provides a process for preparation of the polymeric photochromic comprising reacting a linear or branched poly(C2 to C4 alkylene oxide) optionally comprising terminal linker groups or reactive precursor thereof with a photochromic moiety optionally comprising a linker or reactive precursor thereof.

DETAILED DESCRIPTION

Figure 1:
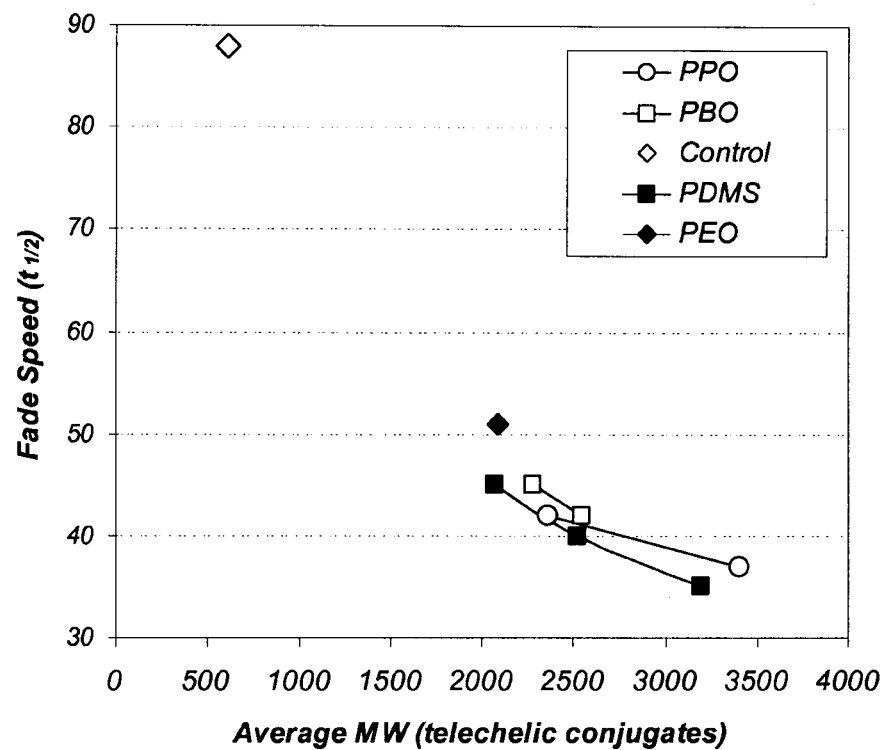
FIG. 1: Plot of the $t_{1/2}$ (seconds) fade speed versus calculated average molecular weights of telechelic naphthopyran-polymer conjugates of the invention and comparative examples (controls). The plot shows that the compounds of the invention are extremely efficient in their ability to increase photochromic fade speed performance within a typical ophthalmic lens matrix formulation, achieving fade speeds comparable to poly(dimethylsiloxane) conjugates known in the prior art (see Malic et al. *Macromolecules*, 2010, 43, 8488 and patent WO 2009/146509 A1) without compromising molecular weight. That is, the amount (mass) of photochromic dye-polymer conjugate of the current invention which would be incorporated within an ophthalmic lens matrix would be comparable to that required of the poly(dimethylsiloxane) conjugates described in the prior art. Legend definitions: PPO=poly(propylene oxide) conjugates (example 1 and 2); PBO=poly(1,2-butylene oxide) conjugates (example 4 and 5); Control=non polymer conjugated dye (comparative example 1); PDMS=poly(dimethylsiloxane) conjugates (comparative examples 2, 3 and 4); PEO=poly(ethylene oxide) conjugate (comparative example 5).
Figure 2:
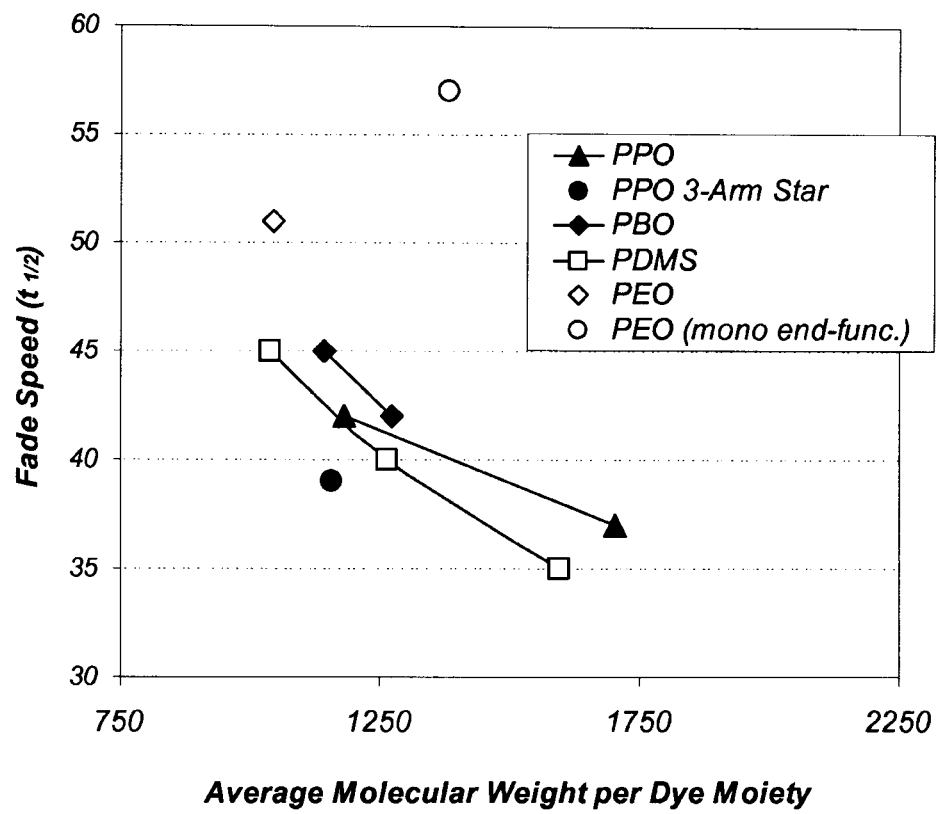
FIG. 2: Plot of the $t_{1/2}$ (seconds) fade speed versus calculated average molecular weights per dye moiety. This plot shows that the 3-arm star architecture (PPO polymer conjugate, Example 3) is an even more efficient system in the enhancement of photochromic fade performance when compared with the linear end-functionalised (telechelic) conjugates, i.e. less polymer is required to achieve the same fade speeds as compared to the linear counterpart. Legend definitions: PPO=poly(propylene oxide) conjugates (example 1 and 2); PPO 3-Arm Star=poly(propylene oxide) conjugate (example 3); PBO=poly(1,2-butylene oxide) conjugates (example 4 and 5); PDMS=poly(dimethylsiloxane) conjugates (comparative examples 2, 3 and 4); PEO=poly(ethylene oxide) conjugate (comparative example 5); PEO (mono end-func.)=poly(ethylene oxide) conjugate (comparative example 6).
Figure 3:
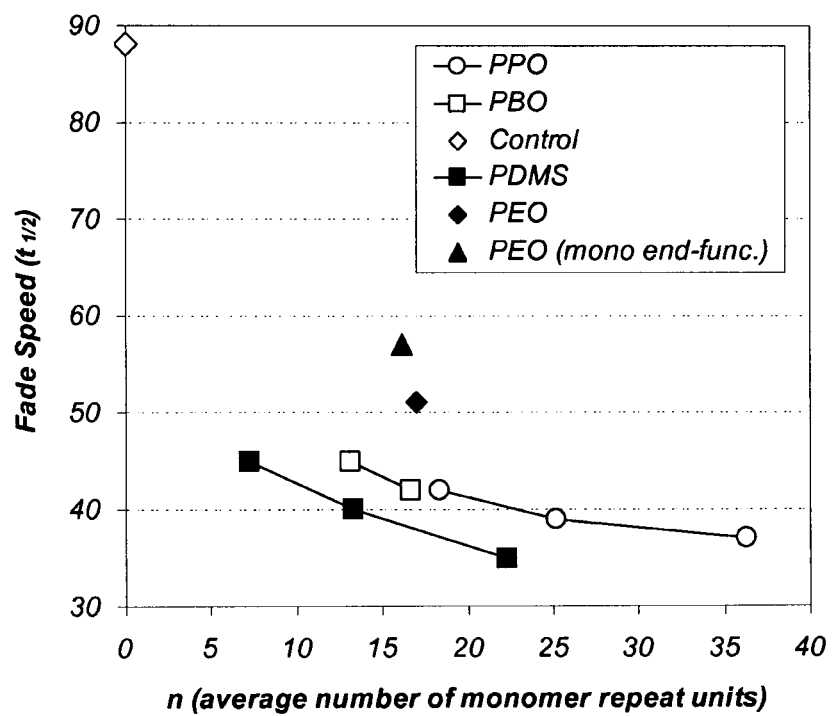
FIG. 3: Plot of the $t_{1/2}$ (seconds) fade speed versus calculated average number of monomer repeat units within the conjugated polymer. This plot gives an overall indication of the fade speed performance of the conjugates based on the chain length. PPO conjugates are shown to require slightly longer chain lengths than PBO and PDMS conjugates to achieve similar photochromic fade speeds. However, as is indicated in FIG. 1, this requirement of longer chain lengths is offset by the lower molecular weight of the monomeric repeat unit of PPO, giving similar overall molecular weights. This plot also displays the tunability of fade speed with molecular weight, higher molecular weight PPO and PBO polymers (longer chains) providing faster fading than shorter chain conjugates. The increase in fade performance moves toward a plateau as molecular weight (monomer repeat units, n) increases, indicating a limit at which further increases in chain length (molecular weight) will not provide any further significant increase in fade speed performance. Legend definitions: PPO=poly(propylene oxide) conjugates (example 1 and 2); PBO=poly(1,2-butylene oxide) conjugates (example 4 and 5); Control=non polymer conjugated dye (comparative example 1); PDMS=poly(dimethylsiloxane) conjugates (comparative examples 2, 3 and 4); PEO=poly(ethylene oxide) conjugate (comparative example 5); PEO (mono end-func.)=poly(ethylene oxide) conjugate (comparative example 6).

The photochromic polymer comprises at least two photochromic moieties linked by a straight or branded chain polymer selected from the group consisting of poly($C_2$ to $C_4$ alkylene oxide) and poly[($C_1$ to $C_{10}$ alkoxy substituted ($C_2$ to $C_4$ alkylene oxide)].

The poly($C_2$ to $C_4$ alkylene oxide) may be an ethylene oxide homopolymer, propylene oxide homopolymer, butylene oxide homopolymer or copolymer of two or more thereof. Preferred poly($C_2$ to $C_4$ alkylene oxide) are poly(propylene oxide), poly(butylene oxide) and copolymers of at least one of propylene oxide and butylene oxide with at least one of ethylene oxide, propylene oxide and butylene oxide. The copolymers include copolymers of ethylene oxide and propylene oxide which may be block copolymers, copolymers of butylene oxide with ethylene oxide which may be block copolymers, copolymers of butylene oxide with propylene oxide which may be block copolymers and copolymers of ethylene oxide, propylene oxide and butylene oxide which may be block copolymers. In one set of embodiments the photochromic polymer comprises a poly(alkylene oxide) polymer which is selected from poly(propylene oxide) and copolymers comprising propylene glycol and one or more of ethylene glycol and butylene glycol. The poly($C_2$ to $C_4$ alkylene oxide) is most preferably poly(propylene oxide).

In one set of embodiments the photochromic polymer is of formula I:

$$(PC\text{-}L\text{-}(RO)_n\text{---})_z X \qquad \text{I}$$

wherein:
Z is from 2 to 8;
PC are independently selected photochromic moieties;
L are independently selected from a bond and linkers;
R are independently selected polymer chains selected from the group consisting of $C_2$ to $C_4$ alkylene and $C_1$ to $C_{10}$ alkoxy substituted ($C_2$ to $C_4$ alkylene);
n is an integer from 1 to 50;
and X is a hydrocarbon comprising from 1 to 20 carbon atoms (preferably of 2 to 6 carbon atoms) or a hydrocarbon ether or polyether of 2, 3 or 4 hydrocarbon units each of 3 to 6 carbon atoms joined through ether linkages and together providing covalent bonds to from 2 to 8 (PC-L-(RO)$_n$—) units.

The hydrocarbon X is bonded to the group poly(alkylene oxide) of each of the groups (PC-L-(RO)$_n$—). The group X may comprise aromatic or aliphatic and is preferably aliphatic of formula:

$$C_m H_{2m+2-z}$$

wherein m is from 1 to 6 and z is as defined for formula I.

Examples of the group X when z is from 2 to 8 include those selected from the group consisting of: ethyl, propyl, butyl. pentyl, and hexyl wherein z is 2

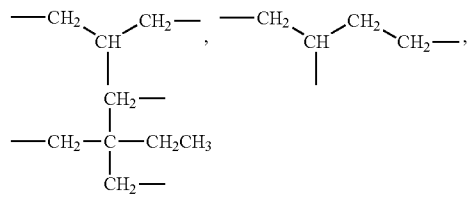

wherein z is 3; and

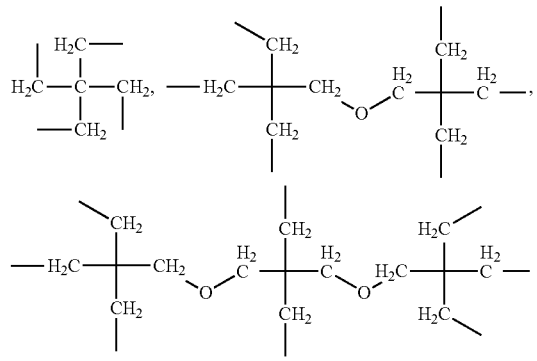

wherein z is from 4, 6 or 8.

In one set of embodiments the photochromic polymer is of formula IIa, IIb or IIc:

$$PC^1\text{-}L^1\text{-}(R^aO)_{n1}\text{---}X^1\text{---}(OR^b)_{n2}\text{-}L^2\text{-}PC^2 \qquad \text{IIa}$$

wherein $X^1$ is selected from the group consisting of ethyl, propyl, butyl, pentyl and hexyl; and

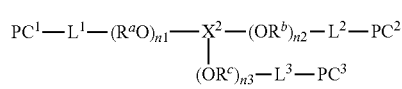

wherein $X^2$ is of formula $C_m H_{2m-1}$ (straight or branched chain) wherein m is from 1 to 6 and preferably $X^2$ selected from:

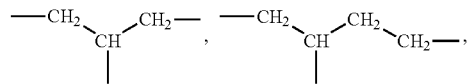

-continued

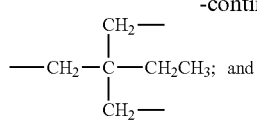
and

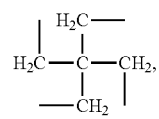

$$PC^1-L^1-(R^a)_{n1}-X^3 \begin{matrix} (OR^d)_{n4}-L^4-PC^4 \\ | \\ -(OR^b)_{n2}-L^2-PC^2 \\ | \\ (OR^c)_{n3}-L^3-PC^3 \end{matrix}$$ IIc wherein $X^3$ is of formula $C_mH_{2m-2}$ (straight or branched chain) wherein m is from 1 to 6 and preferably $X^3$ is $PC^1$, $PC^2$ and $PC^3$ and $PC^4$ are defined as for PC;
$L^1$, $L^2$, $L^3$ and $L^4$ are as defined for L;
$R^a$, $R^b$, $R^c$ and $R^d$ are as defined for R; and
n1, n2, n3 and n4 are from 1 to 20

In one particularly preferred set of embodiments the photochromic polymer is of formula IIa wherein where $(R^aO)_{n1}$ and $(OR^b)_{n2}$ are polypropylene oxide and X is propylene.

Examples of the linker (L) may be selected from the group consisting of:
a bond;

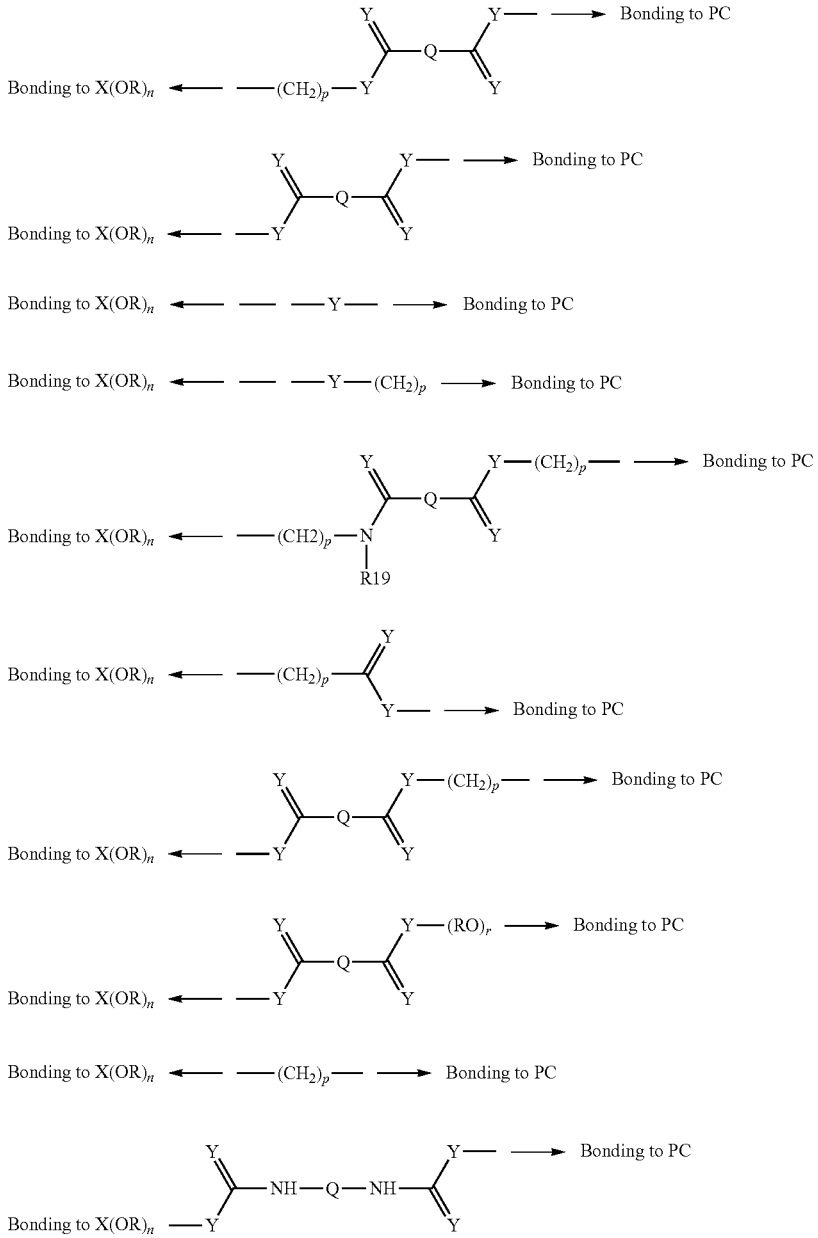

wherein Y is independently NR$^{19}$, oxygen or sulphur, R19 is hydrogen or $C_{1-10}$ alkyl, R20 is $C_{1-10}$ alkyl, p is an integer from 1 to 15, and r is an integer from 0 to 10, and wherein Q is $C_{1-10}$ alkyl (preferably ethyl or propyl), $C_{1-10}$ alkenyl or aryl (preferably 1,2-substituted benzene), optionally further substituted by $C_1$ to $C_{10}$ alkyl, or substituted heteroaryl.

Specific examples of the more linkers (L in formula I and L1, L2, L3 and L4 in formulas IIa, IIb and IIc) include:

[Bonding to X(OR)$_n$]—O—C(O)-Q-C(O)—O—[PC]

[Bonding to X(OR)$_n$]—O—C(O)-Q-C(O)—CH$_2$—CH$_2$—O[PC]

[Bonding to X(OR)$_n$]—O—CH$_2$CH$_2$O—C(O)-Q-C(O)—[PC]

[Bonding to X(OR)$_n$]—O—C(O)-Q-C(O)—[PC]

[Bonding to X(OR)$_n$]—O—CH$_2$—CH$_2$—C(O)-Q-C(O)—O—CH$_2$—CH$_2$—[PC]

[Bonding to X(OR)$_n$]—O—CH$_2$—CH$_2$—C(O)-Q-C(O)—O—CH$_2$—CH$_2$—O—[PC]

wherein [PC] indicates the end bonded to the photochromic, [Bonding to X(OR)$_n$] indicates the end bonded to X(OR)$_n$ and Q is as defined above and is preferably ethyl, propyl or 1,2-substituted benzene.

Specific examples of suitable polyalkylene oxide straight and branched polymers and the resulting photochromic polymers are shown in (i) to (x) below:

(i) poly propylene oxide

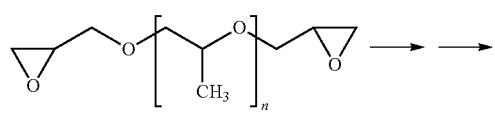

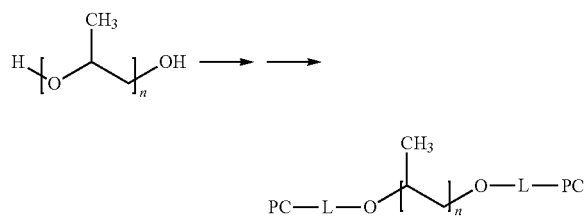

wherein n is from 1 to 60 and preferably from 1 to 30;
(ii) poly(propylene oxide) bis(2-aminopropyl ether)

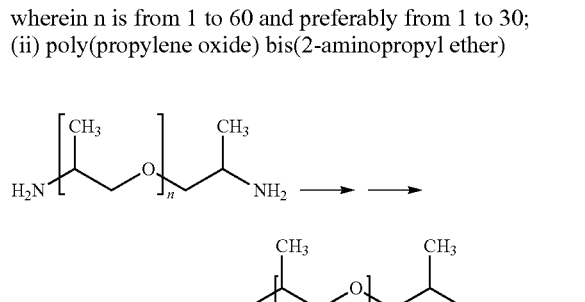

wherein n is from 3 to 60 and preferably from 3 to 30;
(iii) poly(propylene oxide) diglycidyl ether

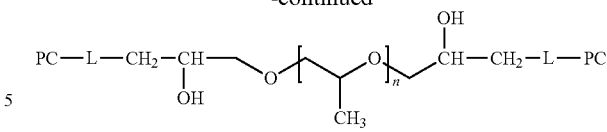

wherein n is from 3 to 60 and preferably from 3 to 30;
(iv) Poly(propylene oxide)-block-poly(ethylene oxide)-block-poly(propylene oxide)

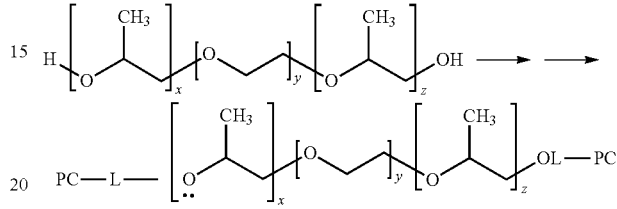

wherein x, y and z are each independently from 1 to 20;
(v) Glycerol tris[poly(propylene oxide), amine terminated] ether

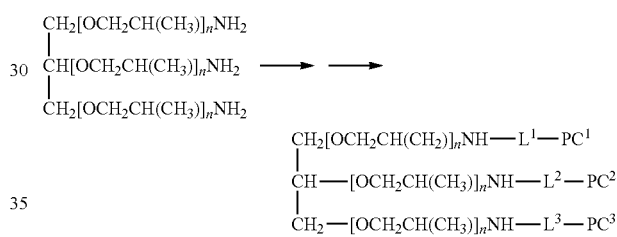

wherein n are each independently from 1 to 20;
(vi) Trimethylolpropane tris[poly(propylene oxide), amine terminated] ether

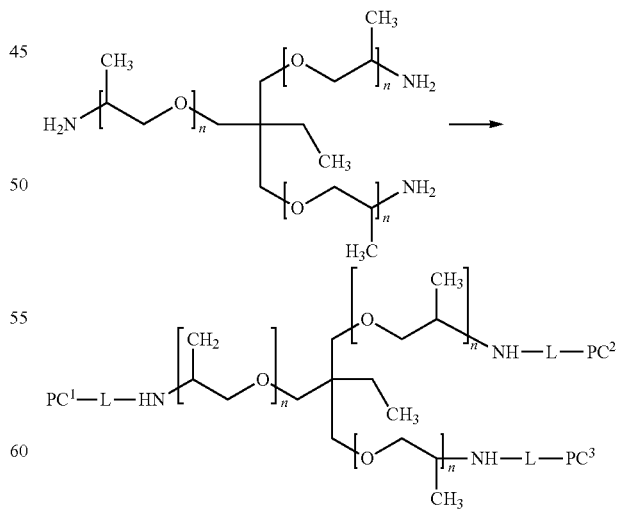

wherein x y and z are each independently from 1 to 20;
(vii) Poly(propylene oxide), tolylene 2,4-diisocyanate terminated

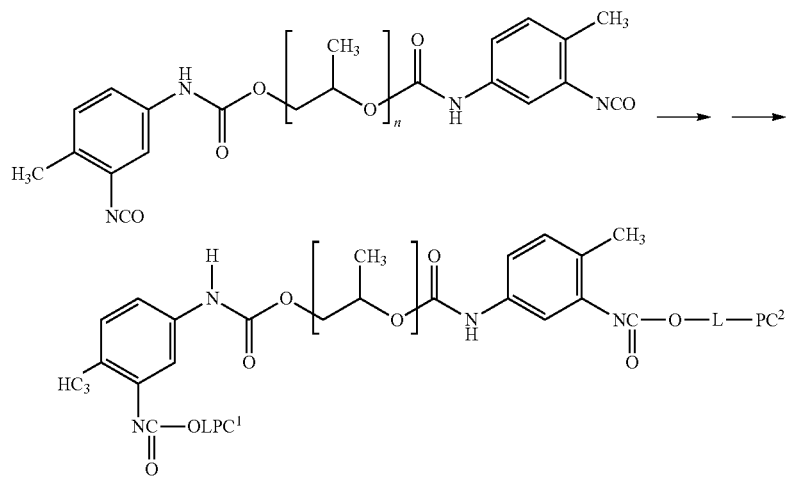

wherein n is from 3 to 60 and preferably from 3 to 30;

(viii) Ethylene oxide,propylene oxide block copolymers

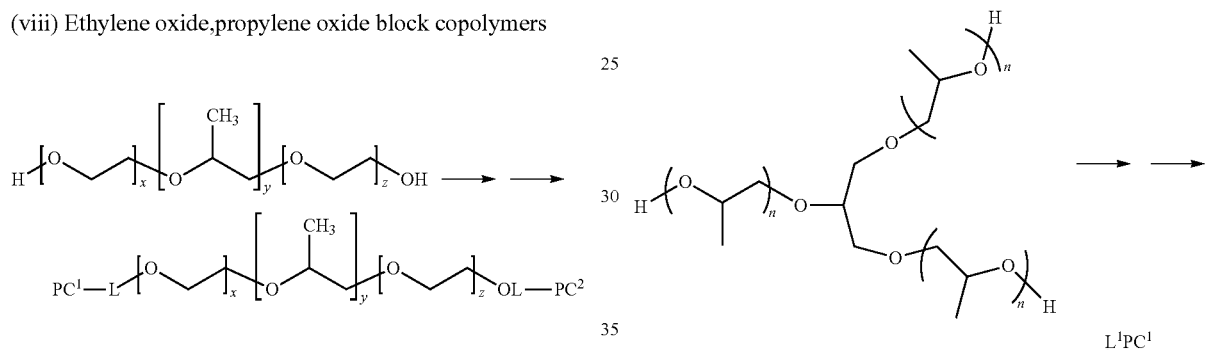

wherein x y and z are each independently from 1 to 20;

(ix) Poly(1,2-butylene oxide)

wherein n is from 3 to 60 and preferably from 3 to 30;

(x) Poly(alkoxy substituted propylene oxide)

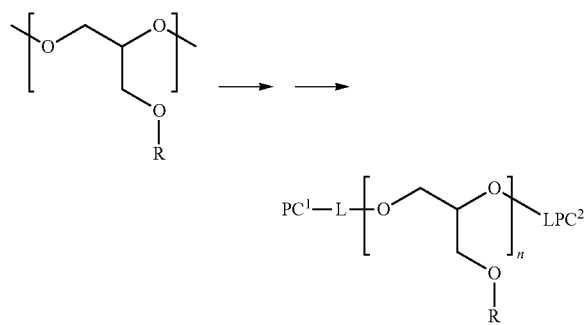

R=$C_1$ to $C_{10}$ alkyl or $C_1$ to $C_{10}$ alkylcarbonyl
wherein n is from 3 to 60.

The photochromic polymers comprise the straight or branched chain polymers which covalently link two or more photochromic moieties. The photochromic moieties are typically located at the terminal of a polymer chain and in the case of branched polymers are preferably located at the terminal of the branches. In one set of embodiments the polymers in the form of a branched polymer having 3 or more branches radiating, for example from hydrocarbon group X and having terminal photochromic moieties.

The photochromic moieties are covalently linked (optionally through a linker such as L) to the polymer.

In a preferred set of embodiments the photochromic moieties are independently selected from the group consisting of naphthopyrans, spiropyrans and spirooxazines.

The photochromic polymer preferably comprises two or more photochromic moieties independently selected from the moieties of formula IIIa to IIId:

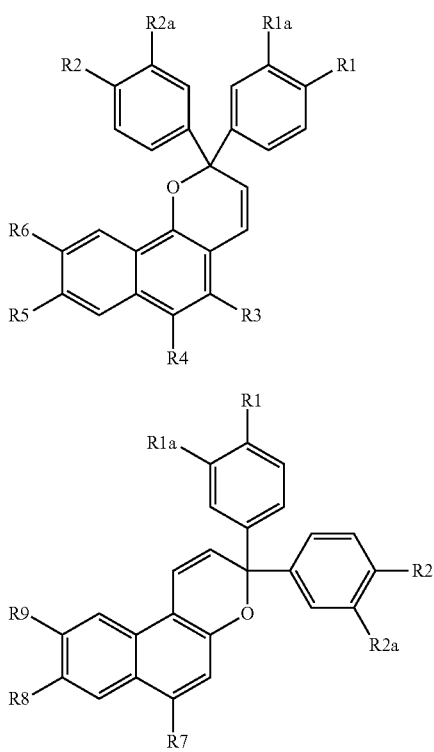

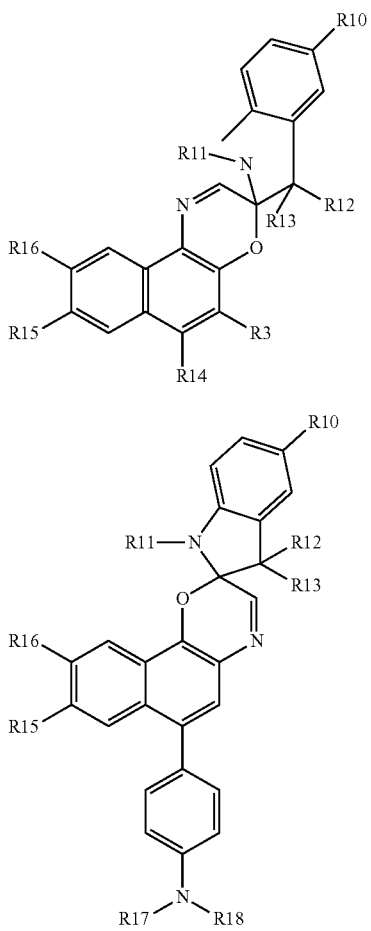

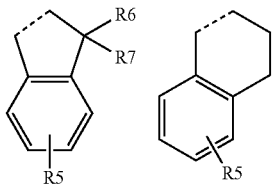

wherein R1 and R2 independently represent hydrogen, $C_{1-10}$ alkyl, $C_{1-10}$ alkoxy, $C_{1-10}$ hydroxyalkoxy, $C_{1-10}$ alkoxy($C_{1-10}$)alkoxy, phenyl, $C_{1-10}$ alkoxyphenyl, halogen $C_{1-5}$ haloalkyl, $C_{1-5}$ alkylamino, $C_{1-5}$ dialkylamino, arylamino, diarylamino, aryl $C_{1-5}$ alkylamino, or a cyclic amino group;

R1a and R2a are hydrogen or together with R1 and R2 respectively may form a carbocyclic or heterocyclic ring of 5 or 6 constituent ring members and optionally up to two heteroatoms selected from oxygen, sulfur and —N(R19)- wherein R19 is selected from hydrogen and $C_{1-10}$ alkyl;

R3 represents hydrogen, $C_{1-10}$ alkyl, up to $C_{20}$ cycloalkyl, up to $C_{20}$ bicycloalkyl, $C_{2-10}$ alkenyl, $C_{1-10}$ alkoxy, $C_{1-10}$ hydroxyalkyl, $C_{1-10}$ alkoxy ($C_{1-10}$) alkyl, $C_{1-10}$ aminoalkyl, $C_{1-20}$ alkoxycarbonyl, carboxyl, halogen, aryloxycarbonyl, formyl, acetyl or aroyl;

R4 represents, phenyl, $C_{1-10}$ alkoxyphenyl, $C_{1-10}$ dialkoxyphenyl, $C_{1-10}$ alkylphenyl, $C_{1-10}$ dialkylphenyl or one of the groups specified for R3;

or R3 and R4 together form a cyclic structure of the type

R5, R6, R7, R8, R9, R10, R14, R15, R16 are as defined for R1 and R2; and

R11 represents linear or branched $C_{1-10}$ alkyl, $C_{1-10}$ hydroxyalkyl, or together form a $C_{5-7}$ ring.

Examples of photochromic compounds which may be used in preparation of the photochromic moiety are disclosed in U.S. Pat. No. 5,446,151, U.S. Pat. No. 5,650,098, U.S. Pat. No. 5,623,005, U.S. Pat. No. 6,303,672 and International Application publication No. WO 2009/146509.

Specific examples of the polymers of formula I include those wherein the photochromic moieties (PC) are independently selected from the group consisting of (a) 1,3-dihydro-3,3-dimethyl-1-neopentyl-6'-(4"-N-ethyl, N-(hydroxylethyl)anilino)spiro[2H-indole-2,3'-3H-naphtho[1,2-b][1,4]oxazine;

(b) 3-(4'-methoxyphenyl),3-(4"-(hydroxyethoxy)phenyl)-6-morpholino-3H-naphtho[2,1-b]pyran;

(c) 3-(4'-methoxyphenyl),3-(4"-(hydroxyethoxy)phenyl)-6-morpholino-3H-naphtho[2,1-b]pyran;

(d) 1,3-dihydro-3,3-dimethyl-1-isobutyl-9'-hydroxy-sprio[2H-indole-2,3'-3H-naphtho[2,1-b][1,4]oxazine;

(e) 2-(4'-pyrrolidinophenyl)-2-phenyl-5-hydroxymethyl-6-anisyl-9-methoxy-2H-naphtho[1,2-b]pyran;

(f) 2,2-bis(4'-methoxyphenyl)-5-hydroxymethyl-6-methyl-2H-naphthol[1,2-b]pyran;

(g) (2-(4'-pyrrolidinophenyl)-2-phenyl-5-hydroxymethyl-6-anisyl-9-methoxy-2H-naphtho[1,2-b]pyran;

(h) 3-phenyl-3-(4'-(hydroxyethoxy)phenyl)-6-morpholino-3H-naphtho[2,1-b]pyran;

(i) 1,3-dihydro-3,3-dimethyl-1-neopentyl-9'-hydroxy-spiro[2H-indole-2,3'-3H-naphthol[2,1-b][1,4]oxazine; and (j) 2,2-Bis(4'-methoxyphenyl)-5-hydroxymethyl-6-methyl-2H-naphtho[1,2-b]pyran.

More specific examples of the photochromic polymer include compounds of formula (i) to (x) wherein PC1, PC2 and PC3 (when present) are selected from one or more of (a) to (j).

In a particularly preferred set of embodiments the straight or branched chain polymer comprises a poly($C_2$ to $C_4$ alkylene oxide) selected from poly(propylene oxide) and copolymers of propylene oxide with one or both of ethylene oxide and butylene oxide and having a molecular weight in the range of from 200 to 10,000 (preferably from 400 to 5,000).

The photochromic polymer may be prepared by attaching the linking group to the polyalkyleneoxide straight or branched chain polymer and reacting the linking group terminated polymer with the photochromic compound. Alternatively, though generally less preferably the linker may be reacted with the photochromic and the linker photochromic adduct then reacted with the straight or branched chain polyalkylene oxide to provide the photochromic polymer.

The linker group in one set of embodiments is reacted with an anhydride precursor to the linker comprising the group of formula (CY)-Q-(CY) such as succinic or phthalic anhydride to provide a straight or branched chain polyalkylene oxide comprising terminal succinic anhydride/acid groups or phthalic anyhydride/acid groups. For example a linear polyalkylene oxide chain may provide a bis-anhydride/acid substituted polyalkylene oxide and a branched polyalkylene oxide having three or more branch arms may provide a tris- or higher terminally anhydride/acid substituted branched polyalkylene oxide. In some embodiments it may be preferred to in addition provide a hydroxyl, amine or acid group of a photochromic to be covalently linked to the polyalkylene oxide with a glycol functionality such as hydroxy ethyl substituted alcohol, ester or amine.

The photochromic polymers preferably have a Tg (glass transition temperature) of less than 25° C., more preferably less than 0° C. and still more preferably a temperature less than minus 25° C. (−25° C.).

In a further set of embodiments there is provided a photochromic polymeric composition comprising a host polymer matrix and the photochromic polymer described above.

In one embodiment the photochromic is incorporated into a polymer resin or polymer resin precursor. The photochromic polymer may be incorporated into a polymer matrix under a range of curing conditions which will be readily appreciated by those skilled in the art having regard to the compositions disclosed above. Typical curing conditions may involve the use of suitable catalysts and or sensitizers. Examples of curing conditions include thermal curing and photopolymerisation. Monomer compositions of the present invention may be applied to a substrate to be rendered photochromic by coating (and subsequent curing) or the compositions may be shaped, for example by casting before thermal or radiation curing. Solvents or carriers may be used to facilitate application of the monomer composition as a coating. Typically the VOC (volatile organic solvent component) will comprise from 0 to 50% by weight of the composition.

The polymerisable composition according to the present invention may include a polymerisation curing agent.

The polymerisation curing agent may be selected from one or more of a UV curable (photo) initiator, radical heat cationic or radical initiator. UV photoinitiation and thermal initiation are preferred. The compositions may be cured by a combination of UV radiation and heat.

The amount of curing agent may vary with the monomers selected. It has been possible to operate with a relatively low level of curing agent of between approximately 0.05 and 4%, preferably 0.05% to 3.0% by weight.

Suitable curing agents may be selected from the group consisting of azodiisobutyronitrile, AIBN (azo radical heat initiator), 2,2'-azobis(N,N'-dimethyleneisobutyramidine)dihydrochloride, 2,2'-azobis(2-amidinopropane)-dihydrochloride, 2,2'-azobis(N,N'-dimethyleneisobutyramidine), 4,4'-azobis(4-cyanopentanoic acid), 2,2'-azobis{2-methyl-N[1,1-bis(hydroxymethyl)-2-hydroxyethyl]propionamide}, 2,2'-azobis{2-methyl-N-[1,1-bis(hydroxymethyl)-ethyl] propionamide}, 2,2'-azobis[2-methyl-N-(2-hydroxyethyl) propionamide], 2,2'-azobis(isobutyramide)dihydrate, 2,2'-azobis(4-methoxy-2,4-dimethylvaleronitrile), 2,2'-azobis(2,4-dimethylvaleronitrile), 2,2'-azobisisobutyronitrile, dimethyl 2,2'-azobis-isobutyrate, 2,2'-azobis(2-methyl-butyronitrile), 1,1'-azobis(1-cyclohexanecarbonitrile), 2-(carbamoylazo)-isobutyronitrile, 2,2'-azobis(2,4,4-trimethylpentane), 2-phenylazo-2,4-dimethyl-4-methoxyvaleronitrile, 2,2'-azobis(2-methylpropane), Trigonox TX-29 (dialkyl peroxide radical heat initiator), 1,1-di-(-butyl peroxy-3,3,5-trimethyl cyclohexane), TBPEH (alkyl perester radical heat initiator), t-butyl per-2-ethylhexanoate (diacyl peroxide radical heat initiator), benzoyl peroxide, (peroxy dicarbonate radical heat initiator), ethyl hexyl percarbonate (ketone peroxide radical heat initiator), methyl ethyl ketone peroxide, "Cyracure UV1-6974" (cationic photoinitiator), triaryl sulfonium hexafluoroantimonate, Lucirin TPO (radical photoinitiator), 2,4,6-trimethylbenzoyidiphenylphosphine oxide, Irgacure 819, bis(2,4,6-trimethylbenzoyl)-phenyl-phosphine oxide, 1-bis(2,6-dimethoxybenzoyl)-2,4,4-trimethylpentyl phosphineoxide, Vicure 55 (radical photoinitiator), methyl phenylglycoxylate, bis(t-butylperoxide)-diisopropylbenzene, t-butyl perbenzoate, t-butyl peroxy neodecanoate, Amicure DBU, Amicure BDMA, DABCO, polycat SA-1, polycat SA-102, polycat SA-610/50, aluminium acetyl acetonate, dibutyltin dilaurate, dibutyltin oxide, Darocur 1173, Irgacure 184, Irgacure 500, Irgacure 1800 and Irgacure 1850.

The initiator may be a single component or combination of initiator components.

Other additives may be present which are conventionally used in coating compositions such as inhibitors, surfactants, UV absorbers, stabilisers and materials capable of modifying refractive index. Such additives may be selected from the group consisting of levelling agents including 3M FC 430 and 3M FC 431.

Examples of surfactants include, fluorinated surfactants or polydimethyl siloxane surfactants such as FC430, FC431 made by 3M, BYK300, BYK371 made by Mallinckrodt, SF-1066, SF-1141 and SF-1188 made by General Electric Company, L-540, L-538 sold by Union Carbide and DC-190 sold by Dow Corning.

Examples of UV absorbers include Ciba Tinuvin P-2(2'-hydroxy-5'methyl phenyl)benzotriazole, Cyanamid Cyasorb UV 531-2-hydroxy-4-n-octoxybenzophenone, Cyanamid Cyasorb UV5411-2(2-hydroxy-5-t-octylphenyl)-benzotriazole, Cyanamid UV 2098-2 hydroxy-4-(2-acryloyloxyethoxyl)benzophenone, National Starch and Chemicals Permasorb MA-2 hydroxy-4-(2 hydroxy-3-methacryloxy) propoxy benzophenone, Cyanamid UV24-2,2'-dihydroxy-4-methoxybenzophenone, BASF UVINUL 400-2,4 dihydroxybenzophenone, BASF UVINUL D-49-2,2'-dihydroxy-4,4' dimethoxy-benzophenone, BASF UVINUL D-50-2,2',4,4' tetrahydroxy benzophenone, BASF UVINUL D-35-ethyl-2-cyano-3,3-diphenyl acrylate, BASF UVINUL N-539-2-ethylhexyl-2-cyano-3,3-diphenyl acrylate, Ciba Geigy Tinuvin 213.

Examples of stabilisers include hydroquinone, coating Solution Stabilizers, nitroso compounds such as Q1301 and Q1300 from Wako Hindered Amine Light Stabilisers (HALS), Including, Ciba Tinuvin765/292bis(1,2,2,6,6)pentamethyl-4-piperidyl)sebacate, Ciba Tinuvin 770-bis(2,2,6,6-tetramethyl-4-piperidinyl)-sebacate.

Examples of antioxidants include Ciba Irganox 245-triethylene glycol-bis-3-(3-tertbutyl-4-hydroxy-5-methyl phenyl) propionate, Irganox 1010-2,2-bis[[3-[3,4-bis(1,1-dimethylethyl)-4-hydroxyphenyl[-1-oxopropoxy]methyl]-1,3-propanediyl 3,5-bis(1,1-dimethyl ethyl)-4-hydroxy benzene propanoate, Irganox 1076-octadecyl 3-(3',5'-di-tert-butyl(-4'-hydroxyphenyl)propionate, hydroquinone, BHT, TBC, MEHQ (4-methoxyphenone), 2-ethoxy-5-(propenyl)phenol, Isoeugenol, 2-allyl phenol, butylated hydroxyanisole.

Examples of anticolouring agents include 10 dihydro-9-oxa-10-phosphaphenanthrene-1-oxide.

Examples of cure modifiers include dodecyl mercaptan, butyl mercaptan, thiophenol.

Examples of nitroso compounds include Q1301 from Wako Nofmer from Nippon Oils and Fats.

Other additives can be present such as viscosity modifiers, and include monomers such as methacrylic acid, vinyl silanes, and other functional monomers. Other monomeric additives may be included to improve processing and/or material properties, these include:

methacrylic acid, maleic anhydride, acrylic acid dye-enhancing, pH-adjusting monomers like Alcolac SIPOMER 2MIM a charge-reducing cationic monomer to render the material more antistatic, example Sipomer Q5-80 or Q9-75.

The composition according to the present invention may be utilised in the preparation of a coated optical article or may be used in casting optical articles.

In a preferred aspect the cured composition exhibits improved scratch resistance when compared with corresponding photochromic articles of comparable fade speed.

The composition of an optical coating may be tailored so that its refractive index substantially matches that of the optical article. The coating may have a thickness in the range of approximately 0.1 to 100 micron (μm).

When the primer coating includes a dye component the primer coating is applied to at least the front (convex) surface of the optical article.

Alternatively, when the primer coating functions to provide improved impact resistance to the optical article, the primer coating preferably has a thickness of approximately 0.7 to 5 micron.

The optical article may be a camera lens, optical lens element, video disc or the like. An optical lens element is preferred.

By the term "optical lens element" we mean all forms of individual refractive optical bodies employed in the ophthalmic arts, including, but not limited to, lenses, lens wafers and semi-finished lens blanks requiring further finishing to a particular patient's prescription. Also included are formers used in the manufacture of progressive glass lenses and moulds for the casting of progressive lenses in polymeric material.

Where the optical article is an optical lens, the optical lenses may be formed from a variety of different lens materials, and particularly from a number of different polymeric plastic resins. Medium to high index lens materials, e.g. those based on acrylic or allylic versions of bisphenols or allyl phthalates and the like are particularly preferred. Other examples of lens materials that may be suitable for use with the invention include other acrylics, other allylics, styrenics, polycarbonates, vinylics, polyesters and the like. Mid to high index lens materials are particularly preferred.

The utilisation of a coating with a mid to high index optical lens is particularly advantageous in improving the impact resistance of the lens. This is particularly so where an antireflective (AR) coating is also included. Such AR coatings may otherwise cause a plastic optical lens to exhibit increased brittleness, for example when heat is applied.

A common ophthalmic lens material is diethylene glycol bis (allyl carbonate). One such material is CR39 (PPG Industries).

The optical article may be formed from cross-linkable polymeric casting compositions, for example as described in the Applicants U.S. Pat. No. 4,912,155, U.S. patent application Ser. No. 07/781,392, Australian Patent Applications 50581/93 and 50582/93, and European Patent Specification 453159A2, the entire disclosures of which are incorporated herein by reference.

For example, in Australian Patent Application 81216/87, the entire disclosure of which is incorporated herein by reference, the Applicant describes a cross-linkable casting composition including at least polyoxyalkylene oxide diacrylate or dimethacrylate and at least one poly functional unsaturated cross-linking agent.

Further, in Australian Patent Application 75160/91, the entire disclosure of which is incorporated herein by reference, describes a polyoxyalkylene oxide diacrylate or dimethacrylate; a monomer including a recurring unit derived from at least one radical-polymerisable bisphenol monomer capable of forming a homopolymer having a high refractive index of more than 1.55; and a urethane monomer having 2 to 6 terminal groups selected from a group comprising acrylic and methacrylic groups.

The polymeric photochromic may be incorporated in the polymer matrix in the process of the present invention by being mixed with a polymerisable monomeric composition that, upon curing produces a solid polymeric composition of Tg typically above 30° C. preferably at least 50° C., still more preferably at least 70° C. and most preferably at least 80° C. The polymerisable composition can be cast as a film, sheet or lens, or injection moulded or otherwise formed into a sheet or lens. Preferably the article will be optically transparent;

(a) The photochromic polymer composition may also be applied to the surface of a material by any convenient manner, such as spraying, brushing, spin-coating or dip-coating from a solution or dispersion of the photochromic material in the presence of a polymeric binder. For example the polymerizable composition (which may be) partly cured) can be dissolved or dispersed in a solvent which can be applied to the surface of a substrate in the form of a permanent adherent film or coating by any suitable technique such as spraying, brushing, spin-coating or dip-coating;

(b) The photochromic polymer composition can be cast or coated onto a substrate by the above mentioned methods and placed within a host material as a discrete layer intermediate to adjacent layers of a host material(s);

(c) The photochromic polymer composition of the invention may be incorporated into a composition by ball milling with a carrier to disperse it in a reactive binder matrix. Such a composition may be used as an ink in ink jet printing and suitable (PC) moieties may be chosen to allow security markings on documents to be visible in exposure to UV light used in photocopy;

(d) The photochromic polymer may be compounded with suitable resins and the resin polymerized with the dye monomer before, during or after being injection moulded to shape it to form a film, for example by blow moulding or to form more complex shaped extruded and/or blown structures.

Examples of host matrix into which the photochromic polymer may be incorporated include homopolymers and copolymers of polyol(allyl carbonate) monomers, homopolymers and copolymers of polyfunctional acrylate monomers, polyacrylates, poly(alkylacrylates) such as poly(methylmethacrylate), cellulose acetate, cellulose triacetate, cellulose acetate propionate, cellulose acetate butyrate, poly(vinyl acetate), poly(vinylalcohol), poly(vinylchloride), poly(vinylidene chloride), polyurethanes, polycarbonates, poly(ethylene-terephthalate), polystyrene, copoly(styrene-methylmethacrylate), copoly(styrene-acrylateonitrile), poly(vinylbutyral), and homopolymers and copolymers of diacylidene pentaerythritol, particularly copolymers with polyol(allylcarbonate) monomers, e.g. diethylene glycol bis (allyl carbonate), and acrylate monomers. Transparent copolymers and blends of the transparent polymers are also suitable as host materials.

The resulting matrix material may be an optically clear polymerized organic material prepared from a polycarbonate resin, such as the carbonate-linked resin derived from bisphenol A and phosgene which is sold under the trademark LEXAN; a poly(methylmethacrylate), such as the material sold under the trademark PLEXIGLAS; polymerizates of a polyol(allyl carbonate), especially diethylene glycol bis(allyl carbonate), which is sold under the trademark CR-39, and its copolymers such as copolymers with vinyl acetate, eg copolymers of from about 80-90 percent diethylene glycol bis(allyl carbonate) and 10-20 percent vinyl acetate, particularly 80-85 percent of the bis(allyl carbonate) and 15-20 percent vinyl acetate, cellulose acetate, cellulose propionate, cellulose butyrate, polystyrene and copolymers of styrene with methyl methacrylate, vinyl acetate and acrylonitrile, and cellulose acetate butyrate.

Polyol (allyl carbonate) monomers which can be polymerised to form a transparent host material are the allyl carbonates of linear or branched aliphatic glycol bis(allyl carbonate) compounds, or alkylidene bisphenol bis(allyl carbonate) compounds. These monomers can be described as unsaturated polycarbonates of polyols, eg glycols. The monomers can be prepared by procedures well known in the art, e.g., U.S. Pat. Nos. 2,370,567 and 2,403,113. The polyol (allyl carbonate) monomers can be represented by the graphic formula:

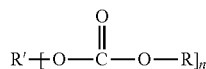

wherein R is the radical derived from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

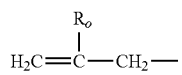

wherein $R_0$ is hydrogen, halogen, or a $C_1$-$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group:

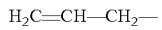

R' is the polyvalent radical derived from the polyol, which can be an aliphatic or aromatic polyol that contains 2, 3, 4 or 5 hydroxy groups. Typically, the polyol contains 2 hydroxy groups, ie a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, ie ethylene glycol, propylene glycol, trimethylene glycol, tetramethylene glycol, or diethylene glycol, triethylene glycol etc.

In a further embodiment, the invention provides a photochromic article comprising a polymeric organic host material selected from the group consisting of poly(methyl methacrylate), polyethylene glycol bismethacrylate), poly(ethoxylated bisphenol A dimethacrylate) thermoplastic polycarbonate, poly(vinyl acetate), polyvinylbutyral, polyurethane, and polymers of members of the group consisting of diethylene glyco bi(allylcarbonate) monomers, diethylene glycol dimethacrylate monomers, ethoxylated phenol bismethylacrylate monomers, diisopropenyl benzene monomers and ethoxylated trimethylol propane triacrylate monomers, and a photochromic polymer covalently tethered to the matrix via a terminal group reactive with the host.

The polymeric matrix material is selected from the group consisting of polyacrylates, polymethacrylates, poly($C_1$-$C_{12}$) alkyl methacrylates, polyoxy(alkylene methacrylates), poly (alkoxylates phenol methacrylates), cellulose acetates, cellulose triacetate, cellulose acetate propionate, cellulose acetate butyrate, poly(vinyl acetate), poly(vinyl alcohol), poly(vinyl chloride) poly(vinylidene chloride), thermoplastic polycarbonates, polyesters, polyurethanes, polythiourethanes, polyethylene terephthalate), polystyrene, poly(alpha methyl styrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methylacrylate monomers, diethylene glycol dimethacrylate monomers, diisopropenyl benzene monomers, alkoxylated polyhydric alcohol monomers and diallylidene pentaerythritol monomers.

The polymerizable composition of the invention may be in the form of a coating or adhesive and may comprise a binder resin and crosslinker. Binders are primarily responsible for the quality of a paint or lacquer coating. Examples of binders include alkyds, polyesters, amino resins such as melamine formaldehyde, acrylics, epoxies and urethanes. The binder may be thermoplastic or thermosetting in character and max be of molecular weight from 500 to several million. Coating comprising the polymerizable composition of the invention may include a solvent to adjust the viscosity. The viscosity may for example be in the range of from 0.5 to 10 Ps. Pigments and fillers may be used to confer opacity or colour. A coating composition based on the composition of the invention may utilise a range of crosslinking systems such as polyisocyanates for cross linking active hydrogen functional groups such as hydroxy and amine; epoxy/acid; epoxy amine and carbamate melamine. The coating composition may be in two pack form, for example one pack comprising the cross linking agent and another pack comprising a binder, a dye monomer as hereinbefore described and optionally further components such as solvents, pigments, fillers and formulation aids.

The terminal reactive group of the polymerizable composition and the binder component may both comprise groups such as hydroxy, amine, alkylamine, chlorosilane, alkoxy silane epoxy unsaturated, isocyanato and carboxyl for reacting with a monomer component on curing.

In this embodiment one pack comprises the binder component and the other the cross-linker. Typically the binder component will comprise 50 to 90% by weight of the coating composition (more preferably 65 to 90%) and the crosslinker components will comprise from 10 to 50% by weight of the coating composition.

Preferred hydroxyl moieties in the binder component are derived from hydroxy monomers, such as hydroxy alkyl acrylates and (meth)acrylates wherein the alkyl group has the range of 1 to 4 carbon atoms in the alkyl group. Exemplars include hydroxy ethyl (meth)acrylate, hydroxy propyl (meth)acrylate, hydroxy butyl (meth)acrylate or a combination thereof.

The monomer mixture which may be used in preparation of an acrylic binder preferably includes one or more monomers selected from alkyl acrylates and corresponding (meth)acrylates having 1-18 carbon atoms in the alkyl group, such as methyl (meth)acrylate, ethyl (meth)acrylate, propyl (meth)acrylate, isopropyl (meth)acrylate, butyl (meth)acrylate, pentyl (meth)acrylate, hexyl (meth)acrylate, 2-ethyl hexyl (meth)acrylate, nonyl (meth)acrylate, lauryl (meth)acrylate, stearyl (meth)acrylate; cycloaliphatic (meth)acrylates, such as trimethylcyclohexyl (meth)acrylate, and isobutylcyclohexyl (meth)acrylate; aryl (meth)acrylates, such as benzyl (meth)acrylate; isobornyl (meth)acrylate; cyclohexyl (meth)acrylate; glycidyl (meth)acrylate; ethyl hexyl (meth)acrylate, benzyl (meth)acrylate or a combination thereof. Methacrylates of methyl, butyl, n-butyl, and isobornyl are preferred. Other monomers such as styrene, alkyl styrene, vinyl toluene and acrylonitrile may be used in addition.

Amine moieties where directed may be provided by alkyl amino alkyl (meth)acrylates such as tert-butylaminoethyl methacrylate.

The crosslinking component of the coating composition of the present invention preferably includes one or more crosslinking agents having at least two isocyanate groups, such as a polyisocyanate crosslinking agent. Any of the conventional aromatic, aliphatic, cycloaliphatic, isocyanates, trifunctional isocyanates and isocyanate functional adducts of a polyol and a diisocyanate can be used. Typically useful diisocyanates are 1,6-hexamethylene diisocyanate, isophorone diisocyanate, 4,4'-biphenylene diisocyanate, toluene diisocyanate, bis cyclohexyl diisocyanate, tetramethylene xylene diisocyanate, ethyl ethylene diisocyanate, 2,3-dimethyl ethylene diisocyanate, 1-methyltrimethylene diisocyanate, 1,3-cyclopentylene diisocyanate, 1,4-cyclohexylene diisocyanate, 1,3-phenylene diisocyanate, 1,5-naphthalene diisocyanate, bis(4-isocyanatocyclohexyl)-methane and 4,4-diisocyanatodiphenyl ether. Prepolymerised forms of these isocyanates are also commonly used to reduce potential exposure hazard of volatile form.

The photochromic article may comprise a polymeric organic material which is a homopolymer or copolymer of monomer(s) selected from the group consisting of acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethyl propane triacrylates.

The photochromic composition of the invention may contain the photochromic compound in a wide range of concentrations depending on the type of photochromic moiety and its intended application. For example in the case of inks in which high colour intensity is required a relatively high concentration of up to 30 wt % photochromic may be required. On the other hand it may be desirable in some cases such as optical articles to use photochromics in very low concentrations to provide a relatively slight change in optical transparency on irradiation. For example, as low as 0.01 mg/g of matrix may be used. Generally the photochromic resin will be present in an amount of from 0.01 mg/g of matrix up to 30 wt % of host matrix. More preferably the photochromic compound will be present in an amount of from 0.01 mg/g to 100 mg/g of host matrix and still more preferably from 0.05 mg/g to 100 mg/g of host matrix.

The photochromic article may contain the photochromic compound in an amount of from 0.01 to 10.0 milligram per square centimeter of polymeric organic host material surface to which the photochromic substance(s) is incorporated or applied.

The dye monomers and polymerizable compositions of the invention may be used in those applications in which the organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g. coating compositions. The dye monomers and photochromic compositions may also be used as a means of light activated date storage. As used herein, coating compositions include polymeric coating composition prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates, which include paper, glass, ceramics, wood, masonry, textiles, metals and polymeric organic materials. Coating compositions may be used to produce verification marks on security documents, e.g. documents such as banknotes, passport and driver' licenses, for which authentication or verification of authenticity may be desired. Throughout the specification and claims terms are used in the definition of chemical groups and substituents which unless a contrary intent is indicated have the meanings referred to below.

"Alkyl" as a group or part of a group refers to a straight or branched aliphatic hydrocarbon group, of for example one to twenty carbon atoms, preferably a $C_1$-$C_{10}$ alkyl, most preferably $C_1$-$C_6$ alkyl unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group where the context provides.

"Alkyloxy" and "alkoxy" refer to an alkyl-O— group in which alkyl is as defined herein. Preferably the alkoxy is a $C_1$ to $C_6$ alkoxy. Examples include, but are not limited to, methoxy and ethoxy. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_8$ aryl group and most preferably is phenyl.

A "bond" is a linkage between atoms in a compound or molecule. The bond may be a single bond, a double bond, or a triple bond.

"Acryl" refers to a group of formula RC(O)— where R may be, for example, aryl or alkyl. "Acyloxy" refers to the group of formula R C(O)O— where R is alkyl or aryl.

"Halogen" or "halo" represents chlorine, fluorine, bromine or iodine and most preferably fluorine or chlorine.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-bi] thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, Z—, or 3-indolyl, and 2-, or 3-thienyl. A heteroaryl group is typically a $C_1$-$C_{18}$ heteroaryl group. The group may be a terminal group or a bridging group.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom.

Examples of heterocyclic moieties include heterocycloalkyl, heterocycloalkenyl and heteroaryl.

The term switching speed refers to the speed of colouration when a photochromic is exposed to light and also to the speed of fade when a coloured photochromic is removed from the light. The term t½ refers to the time taken for the colour to fade to half the intensity when the photochromic article is removed from light. The term t¾ refers to the time taken for the colour to fade by ¾ of the original intensity when the photochromic article is removed from light.

The invention will now be described with reference to the following examples. It is to be understood that the examples are provided by way of illustration of the invention and that they are in no way limiting to the scope of the invention.

EXAMPLES

Example 1

Step 1

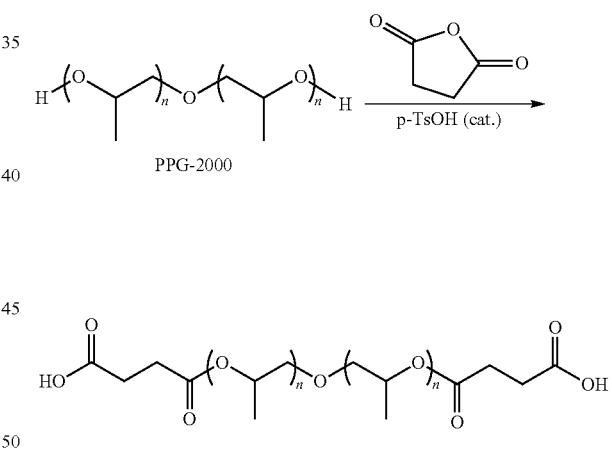

Poly(propylene oxide) (2.52 g, average molecular weight=2,000, Aldrich), succinic anhydride (0.365 g) and p-toluenesulfonic acid (0.05 g) were combined and heated at 125° C. for 30 minutes under nitrogen, with stirring. The mixture was then dissolved in diethyl ether/hexane (4:1) and washed twice with 2M HCl and brine. The organic layer was separated, dried with $MgSO_4$, filtered and the solvent evaporated in vacuo giving the product, bis(succinic acid/ester) end-functionalised poly(propylene oxide), as a viscous oil. Analysis by $^1$H NMR ($CDCl_3$) confirmed the structure and the complete reaction of the hydroxyl end-groups of the starting polymer. The average molecular weight was determined to be 2,444 by analysis of integrations of resonance peaks.

Step 2

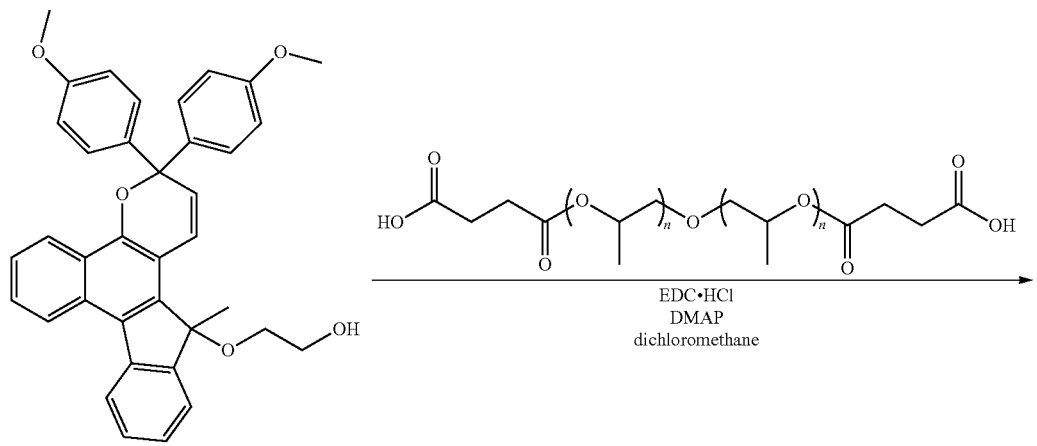

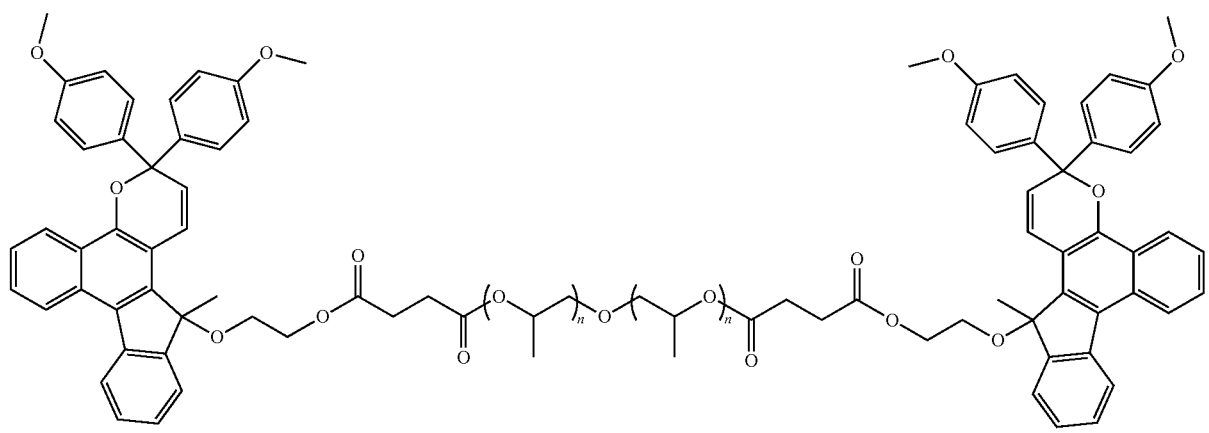

The parent naphthopyran used in this step, 3,3-di(4-methoxyphenyl)-13-hydroxy-13-methyl-indeno[2,1-f]naphtho[1,2-b]pyran, was synthesised using the procedure outlined in U.S. Pat. No. 5,645,767. It's conversion to the 13-(2-hydroxyethoxy) derivative was carried out using the procedure outlined in Malic et al. *Macromolecules,* 2010, 43, 8488.

Bis(succinic acid/ester) end-functionalised poly(propylene oxide) from Step 1 (0.549 g), N-(3-dimethylaminopropyl)-N'-ethylcarbodiimide hydrochloride (EDC.HCl) (0.108 g) and 4-dimethylaminopyridine (DMAP) (0.055 g) were dissolved in dry dichloromethane (ca. 2 mL) under nitrogen. A solution of 3,3-di(4-methoxyphenyl)-13-(2-hydroxyethoxy)-13-methyl-indeno[2,1-f]naphtho[1,2-b]pyran (0.25 g) in dry dichloromethane (ca. 2-3 mL) was then added via syringe and the mixture stirred at ambient temperature for 2.5 hours. The solvent was evaporated and the residue purified by column chromatography (silica gel, diethyl ether), giving the product conjugate as a purple-coloured viscous tar (0.23 g).

Analysis by $^1$H NMR ($d_6$-acetone) confirmed the structure as the (telechelic) bis(naphthopyran succinate) end-functionalised poly(propylene oxide), with an average molecular weight of 3,406 ($n_{PPO}$=36.3) as determined by the integrations of resonance peaks from the polymer backbone versus the naphthopyran termini.

Example 2

Step 1

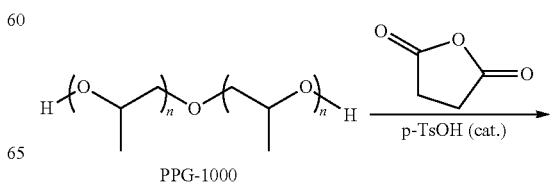

-continued

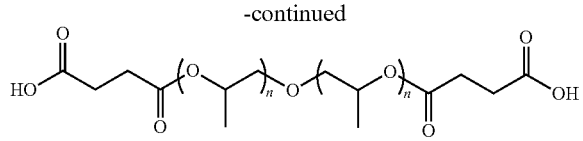

Poly(propylene oxide) (5.02 g, average molecular weight=1,000, Aldrich), succinic anhydride (2.50 g) and p-toluenesulfonic acid (0.13 g) were combined and heated at 130° C. for 30 minutes and then at 80° C. for a further 1.5 hours, under nitrogen with stirring. Poly(ethylene glycol) monomethyl ether (5.25 g, average molecular weight=350, Aldrich) was added and mixture heated at 100° C. for 30 minutes. The mixture was then dissolved in diethyl ether and washed three times with dilute HCl and finally brine. The organic layer was separated, dried with $MgSO_4$, filtered through a plug of silica gel and the solvent evaporated in vacuo giving the product, bis(succinic acid/ester) end-functionalised poly(propylene oxide), as a viscous oil. Analysis by $^1H$ NMR ($CDCl_3$) confirmed the structure and the complete reaction of the hydroxyl end-groups of the starting polymer. The average molecular weight was determined to be 1,264 by analysis of the integrations of resonance peaks.

Step 2

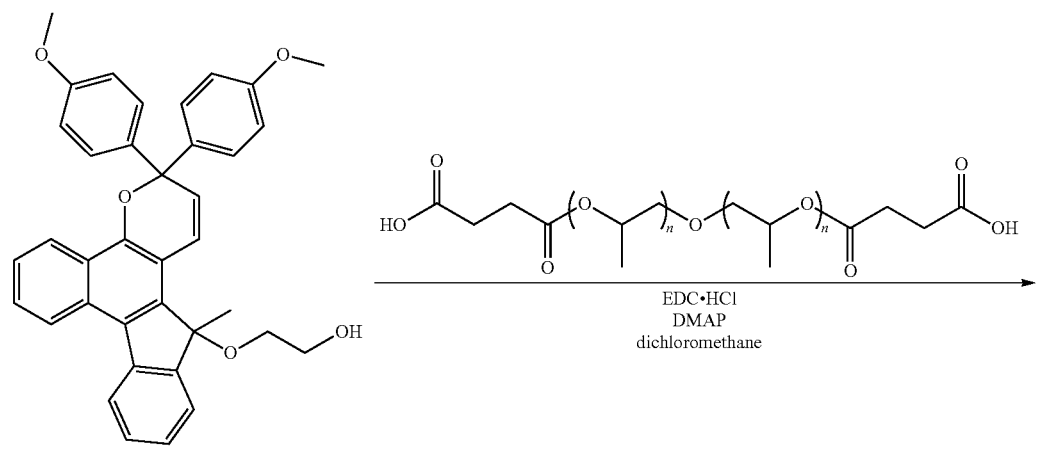

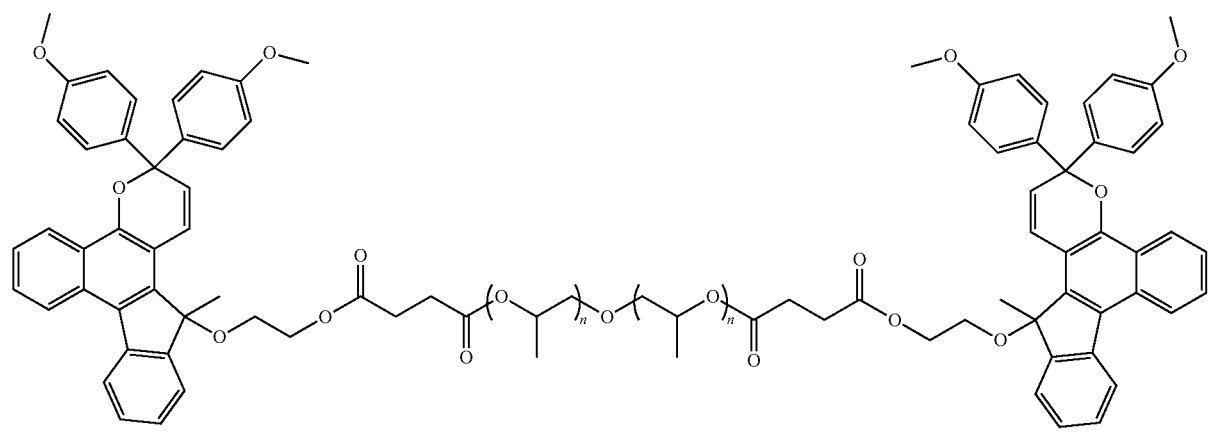

Bis(succinic acid/ester) end-functionalised poly(propylene oxide) from Step 1 (0.227 g), N-(3-dimethylaminopropyl)-N'-ethylcarbodiimide hydrochloride (EDC.HCl) (0.103 g) and 4-dimethylaminopyridine (DMAP) (0.022 g) were dissolved in dry dichloromethane (ca. 3 mL) under nitrogen and stirred for 5 minutes at ambient temperature. 3,3-Di(4-methoxyphenyl)-13-(2-hydroxyethoxy)-13-methyl-indeno[2,1-f]naphtho[1,2-b]pyran (0.20 g, see Example 1, Step 2) was then added as a solid and the mixture stirred for a further 2 hours. The mixture was filtered through a plug of silica gel and the solvent evaporated giving a residue which was then purified by column chromatography (silica gel, diethyl ether), giving the product conjugate as a purple-coloured viscous tar (0.162 g). Analysis by $^1$H NMR ($d_6$-acetone) confirmed the structure as the (telechelic) bis(naphthopyran succinate) end-functionalised poly(propylene oxide), with an average molecular weight of 2,362 ($n_{PPO}$=18.4) as determined by the integrations of resonance peaks from the polymer backbone versus the terminal naphthopyran moieties.

Example 3

Step 1

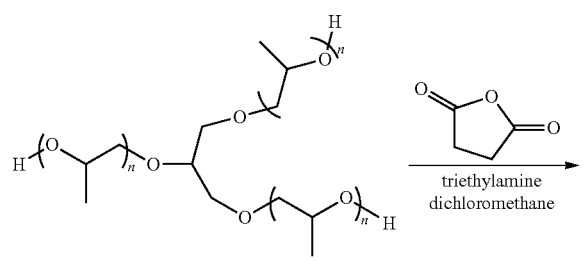

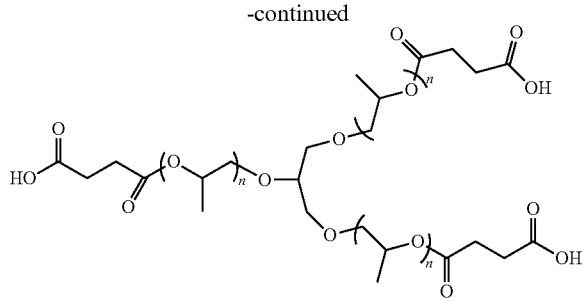

Glycerol propoxylate (5.09 g, average molecular weight=1,500), succinic anhydride (1.50 g) and triethylamine (2.10 mL) were added to dry dichloromethane (ca. 50 mL) under nitrogen and stirred at ambient temperature overnight. Poly(ethylene glycol) monomethyl ether (1.68 g, MW=350) was then added and the mixture stirred for an additional 30 minutes after which the solvent was evaporated in vacuo. The residue was taken up in diethyl ether and washed three times with dilute HCl and finally brine. The organic layer was separated, dried with MgSO$_4$, filtered and the solvent evaporated, giving the product as a viscous oil (5.11 g). Analysis by $^1$H NMR (CDCl$_3$) confirmed the structure as the tris(succinic acid/ester) end-functionalised glycerol propoxylate. The average molecular weight was determined to be 2,175 ($n_{PPO}$=10.2 per arm) by comparison of integrations of resonance peaks corresponding to the polymer backbone versus the terminal succinate groups.

Step 2

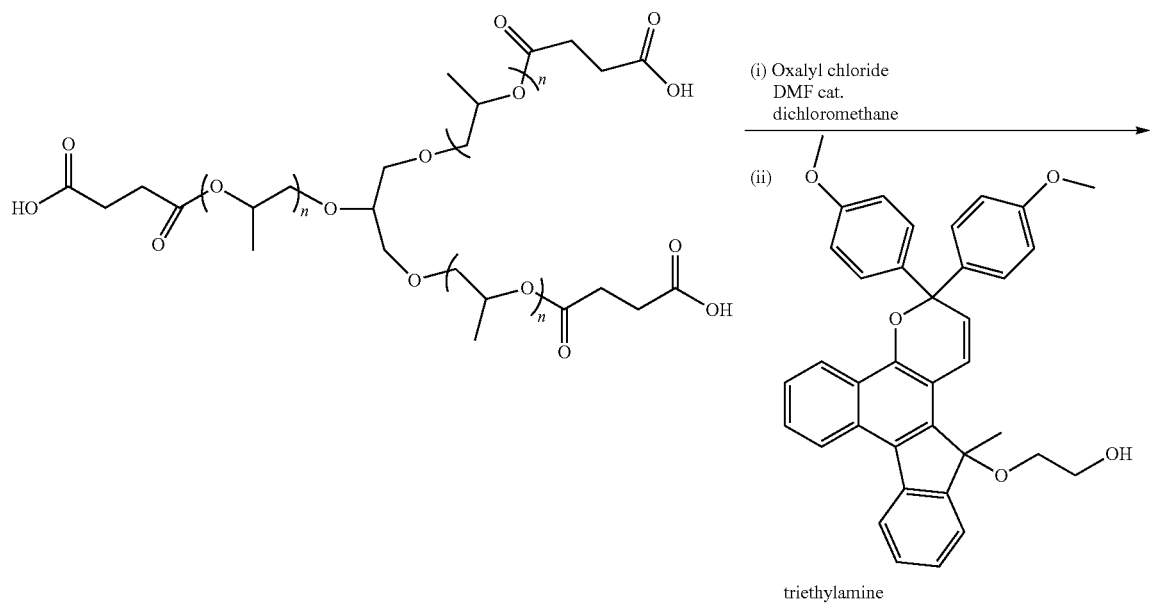

-continued

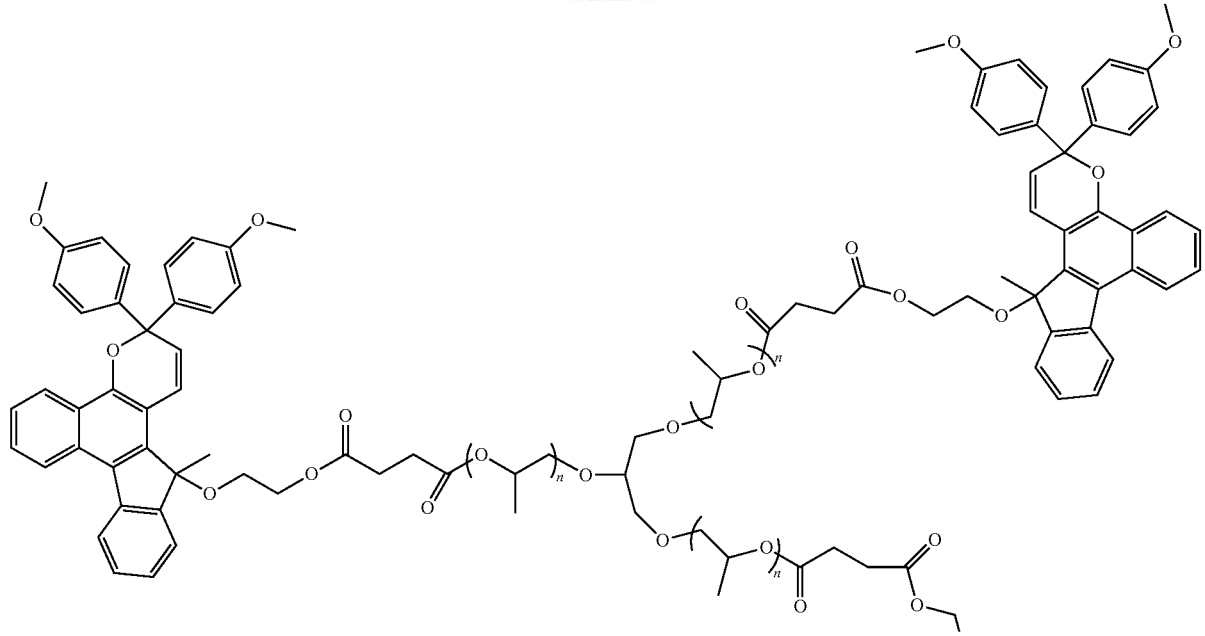

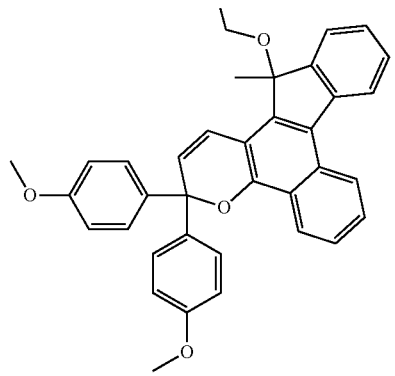

The tris(succinic acid/ester) end-functionalised glycerol propoxylate from Step 1 (0.26 g) was dissolved in dry dichloromethane (ca. 5 mL). To this solution was added 1 small drop of dimethylformamide (DMF) and an excess of oxalyl chloride (0.06 mL, ca. 6 molar equivalents). The mixture was stirred for 30 minutes at ambient temperature, under nitrogen and then the solvent and excess reagent removed in vacuo, giving the tris(succinoyl chloride) terminated glycerol propoxylate. In a separate flask was dissolved 3,3-di(4-methoxyphenyl)-13-(2-hydroxyethoxy)-13-methyl-indeno[2,1-f]naphtho[1,2-b]pyran (0.20 g, see Example 1, Step 2) in dry dichloromethane, to which was added an excess of triethylamine (ca. 0.10 mL) followed by a solution of the tris(acid chloride) terminated glycerol propoxylate in dichloromethane (ca. 2 mL), via syringe. The mixture was stirred at ambient temperature for 30 minutes, under nitrogen. The solvent was then removed in vacuo and the residue purified by column chromatography (silica gel, diethyl ether) giving the product conjugate as a purple-coloured tar (0.16 g). Analysis by $^1$H NMR confirmed the structure as the tris(naphthopyran succinate) end-terminated glycerol propoxylate (naphthopyran succinate terminated poly(propylene oxide) 3-armed star polymer conjugate). The average molecular weight was determined to be 3,475 ($n_{PPO}$=8.4 per arm) by comparison of integrations of resonance peaks corresponding to the polymer backbone versus the terminal naphthopyran groups.

Examples 4 and 5

Step 1

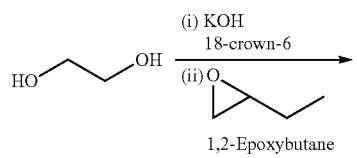

1,2-Epoxybutane

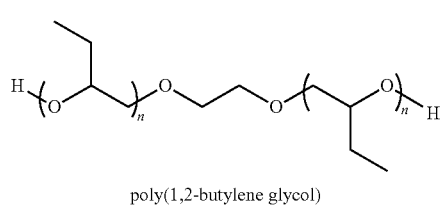

poly(1,2-butylene glycol)

Poly(1,2-butylene oxide) was synthesised using the procedure of Heatley et al. *Eur. Polym. J.* 1990, 26, 583-592.

Anhydrous ethylene glycol (0.621 g), KOH (0.132 g, 15% $H_2O$) and 18-crown-6 ether (0.529 g) were added to a Schlenk flask under nitrogen and stirred with gentle heating until dissolution of all components achieved. Vacuum was applied to the flask and then heated until ethylene glycol began to reflux. The mixture was allowed to cool to ambient temperature and then 1,2-epoxybutane (10.0 g) added via syringe. The homogeneous mixture was stirred at 60° C. for 20 hours giving a viscous brown oil. Glacial acetic acid (0.12 g) was added to quench the reaction and the oil dissolved in diethyl ether, washed with dilute $NaHCO_3$, water and finally brine. The organic layer was dried with $MgSO_4$, filtered through a plug of silica gel and the solvent evaporated in vacuo giving a near colourless oil product (9.49 g). Analysis by $^1H$ NMR ($CDCl_3$) confirmed the structure as poly(1,2-butylene oxide), with an average molecular weight of 1,076 ($n_{PBO}$=14.1) as determined by the integrations of resonance peaks from the polymer backbone versus the termini.

Step 2

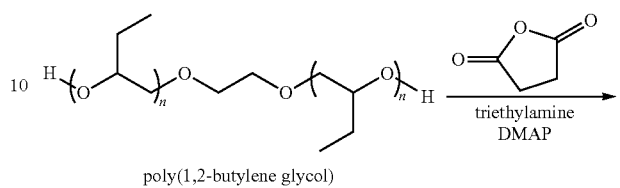

poly(1,2-butylene glycol)

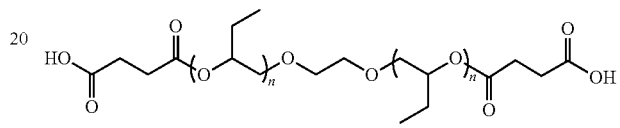

Poly(1,2-butylene oxide) from Step 1 (2.026 g), succinic anhydride (0.558 g), 4-dimethylaminopyridine (0.068 g) and triethylamine (0.52 mL) were dissolved in dry dichloromethane (ca. 5 mL) under nitrogen and stirred at ambient temperature for 17 hours. Poly(ethylene glycol) monomethyl ether (0.60 mL, average molecular weight=350) was added and the mixture stirred for a further 30 minutes, after which the solvent was evaporated in vacuo. The residue was dissolved in diethyl ether and washed 3 times with dilute HCl, then with brine. The organic layer was dried with $MgSO_4$, filtered through a plug of silica gel and the solvent evaporated in vacuo giving the product bis(succinic acid/ester) terminated poly(1,2-butylene oxide), (1.94 g). The product was analysed by $^1H$ NMR ($CDCl_3$) which confirmed the complete reaction of the terminal hydroxy groups and gave an average molecular weight of 1,329 ($n_{PBO}$=14.8) by analysis of the integrations of selected resonance peaks.

Step 3

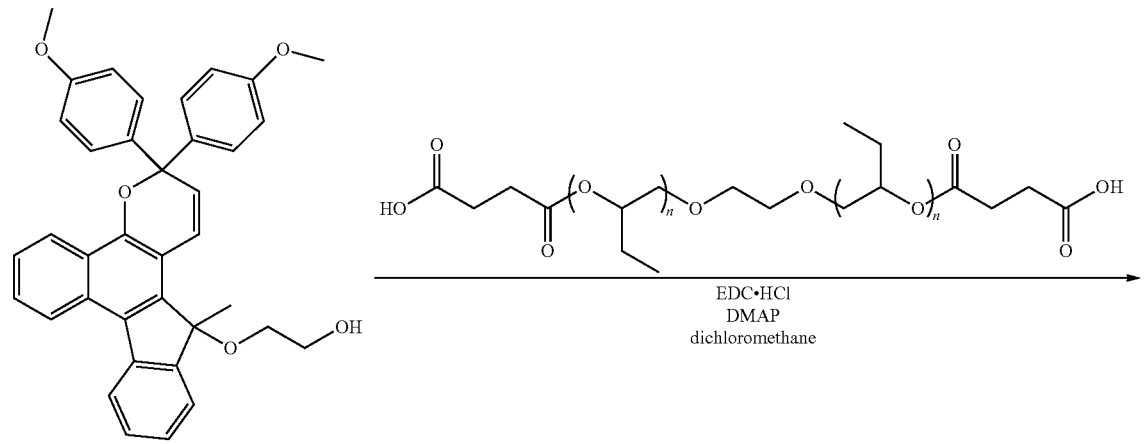

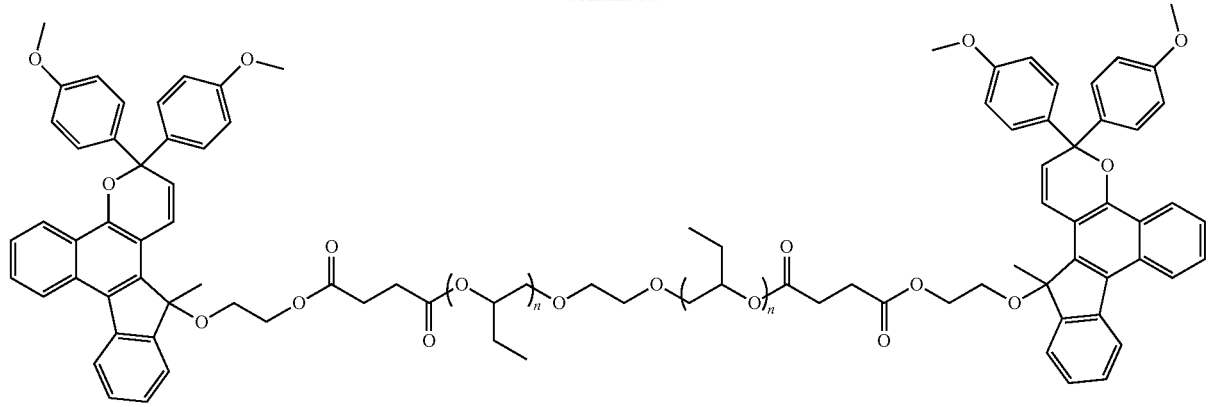

Bis(succinic acid/ester) terminated poly(1,2-butylene oxide) from Step 2 (0.20 g) was dissolved in dry dichloromethane (ca. 3 mL) together with N-(3-dimethylaminopropyl)-N'-ethylcarbodiimide hydrochloride (EDC.HCl) (0.103 g) and 4-dimethylaminopyridine (DMAP) (0.050 g), under nitrogen. This mixture was stirred for 5 minutes at ambient temperature and then 3,3-di(4-methoxyphenyl)-13-(2-hydroxyethoxy)-13-methyl-indeno[2,1-f]naphtho[1,2-b]pyran (0.20 g, see Example 1, Step 2) added as a solid. The mixture was stirred for a further 1.5 hours, the solvent evaporated in vacuo and the residue purified by column chromatography (silica gel, diethyl ether/petroleum ether, 4:1). The single product band was collected as two fractions and then analysed by $^1$H NMR (d$_6$-acetone) which gave average molecular weights of 2,544 ($n_{PBO}$=16.7) and 2,284 ($n_{PBO}$=13.1) for fractions 1 (Example 4) and 2 (Example 5), respectively.

Example 6

1,3-Dihydro-3,3-dimethyl-1-neopentyl-6'-(4''-N-ethyl, N-hydroxyethylanilino)spiro[2H-indole-2,3'-3H-naphtho[1,2-b][1,4]oxazine] (0.25 g) prepared as described in York et al. Synth. Commun. 2010, 40, 3618 or U.S. Pat. No. 6,303,673) is dissolved in dry dichloromethane, under nitrogen, together with bis(succinic acid/ester) end-functionalised poly(propylene oxide) (0.56 g, prepared as described in Example 1, Step 1, 0.5 molar equivalents) and 4-dimethylaminopyridine (6 mg, 0.1 molar equivalents). The mixture is stirred at ambient temperature for 10 minutes before the addition of N-(3-dimethylaminopropyl)-N'-ethylcarbodiimide hydrochloride (EDC.HCl) (0.131 g, 1.5 molar equivalents) followed by additional stirring at ambient temperature for 1 hour. The mixture is filtered through a plug of silica gel, eluting with further portions of dichloromethane. The product conjugate, (1,3-Dihydro-3,3-dimethyl-1-neopentyl-6'-(4''-N-ethyl, N-succinylethylanilino)spiro[2H-indole-2,3'-3H-naphtho[1,2-b][1,4]oxazine])$_2$-poly(propylene oxide), is purified and isolated by column chromatography using silica gel.

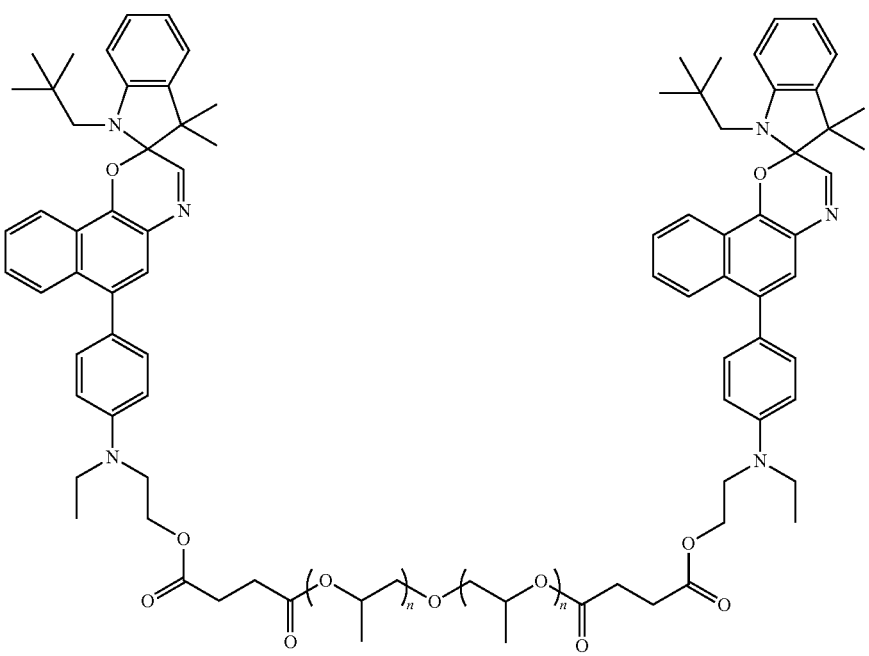

Example 7

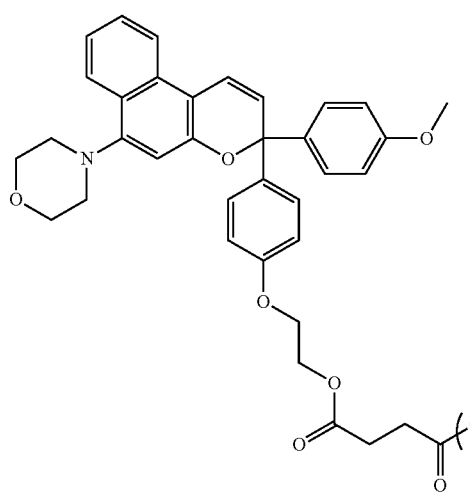
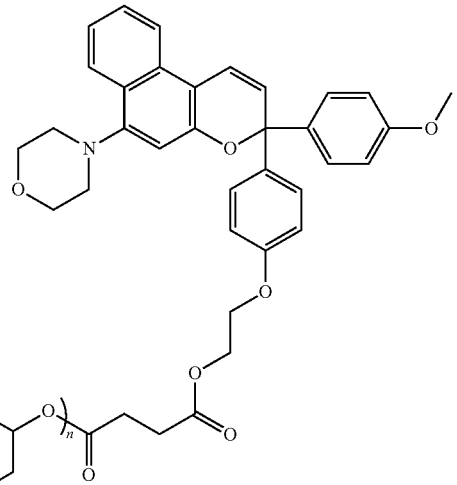

3-(4'-Methoxyphenyl),3-(4"-hydroxyethoxyphenyl)-6-morpholino-3H-naphtho[2,1-b]pyran (0.25 g, prepared as described in U.S. Pat. No. 5,623,005) is dissolved in dry dichloromethane, under nitrogen, together with bis(succinic acid/ester) end-functionalised poly(1,2-butylene oxide) (0.326 g, prepared as described in Examples 4 and 5, Steps 1 and 2; 0.5 molar equivalents) and 4-dimethylaminopyridine (6 mg, 0.1 molar equivalents). The mixture is stirred at ambient temperature for 10 minutes before the addition of N-(3-dimethylaminopropyl)-N'-ethylcarbodiimide hydrochloride (EDC.HCl) (0.141 g, 1.5 molar equivalents) followed by additional stirring at ambient temperature for 1 hour. The mixture is filtered through a plug of silica gel, eluting with further portions of dichloromethane, and the solvent evaporated in vacuo. The residue is then purified and isolated by column chromatography using silica gel, giving the product conjugate, (3-(4'-methoxyphenyl),3-(4"-(succinylethoxy) phenyl)-6-morpholino-3H-naphtho[2,1-b]pyran)$_2$-poly(1,2-butylene oxide).

Example 8

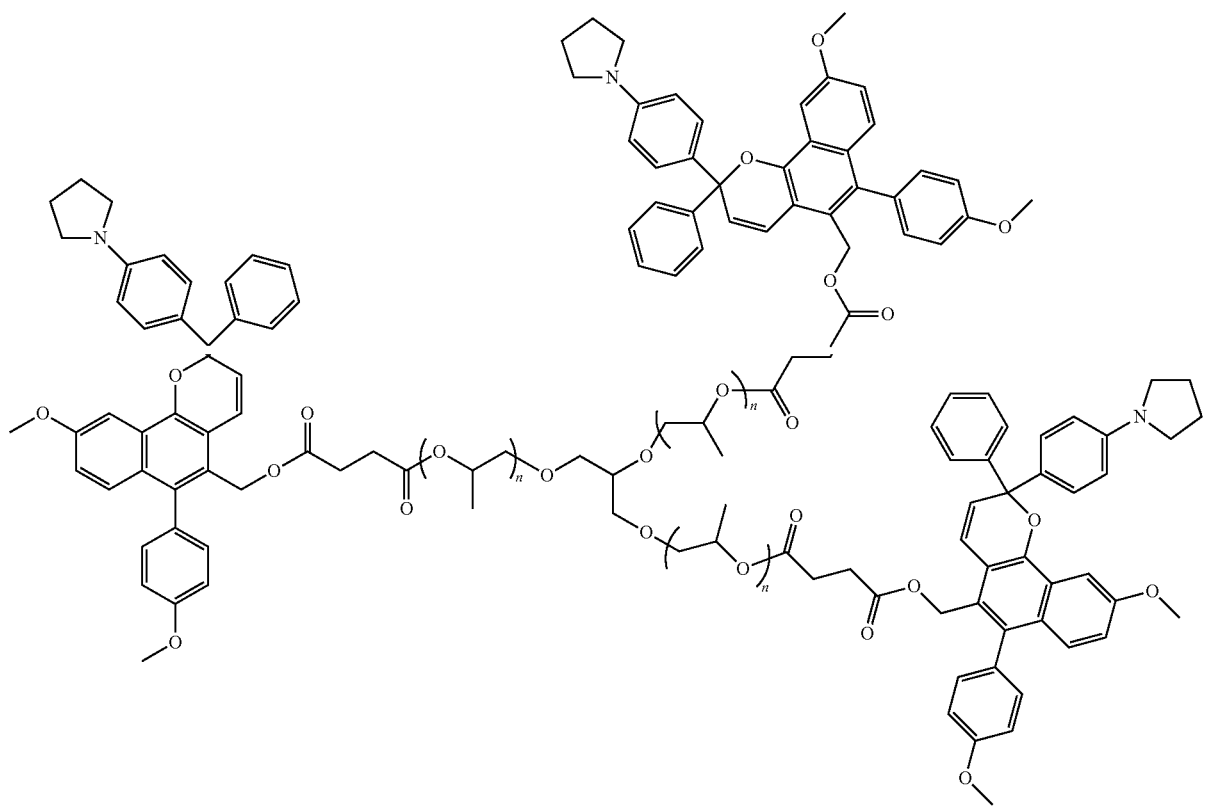

Tris(succinic acid/ester) end-functionalised glycerol propoxylate (0.318 g, prepared as described in Example 3, Step 1) is converted to the tris(succinoyl chloride) end-functionalised glycerol propoxylate using the procedure outlined in Example 3, Step 2. This is then added to a solution comprised of 2-(4'-pyrrolidinophenyl)-2-phenyl-5-hydroxymethyl-6-anisyl-9-methoxy-2H-naphtho[1,2-b]pyran (0.25 g, prepared as described in U.S. Pat. No. 5,650,098; 3 molar equivalents) and triethylamine (ca. 0.12 mL) dissolved in dry dichloromethane, under nitrogen. The mixture is stirred at ambient temperature for 1 hour and the solvent removed in vacuo. The residue is purified by column chromatography giving the product conjugate, (2-(4'-pyrrolidinophenyl)-2-phenyl-5-succinylmethyl-6-anisyl-9-methoxy-2H-naphtho[1,2-b]pyran)$_3$-glycerol propoxylate (ie. naphthopyran end-functionalised poly(propylene oxide) 3-armed star).

Comparative Example 1

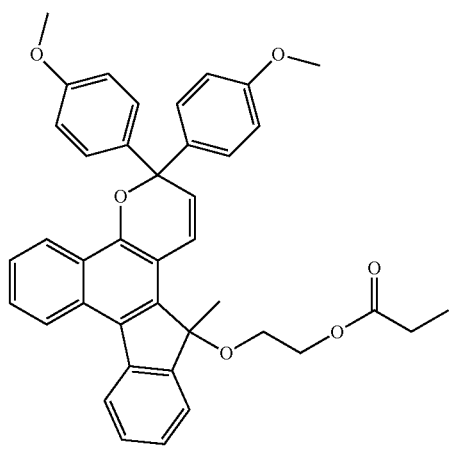

Example 9

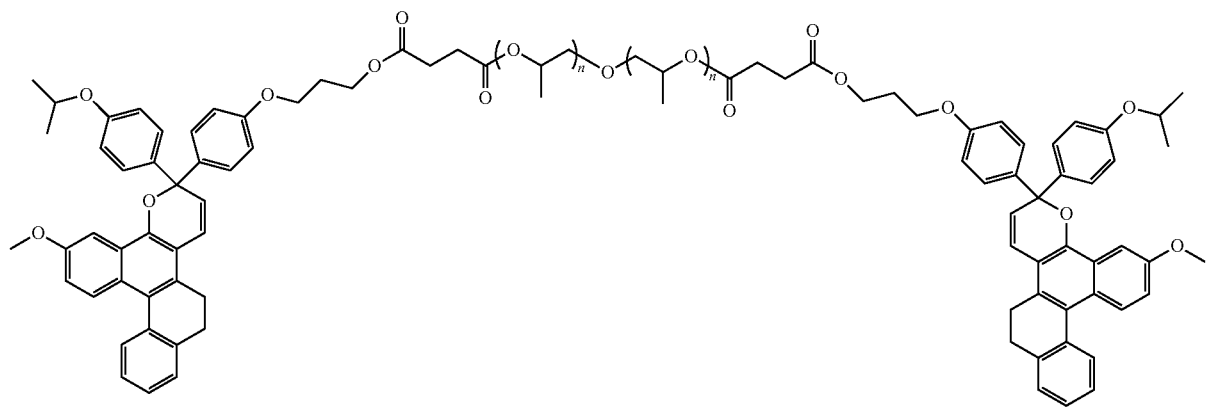

Bis(succinic acid/ester) end-functionalised poly(propylene oxide) (0.510 g, prepared as described in Example 1, Step 1), N-(3-dimethylaminopropyl)-N'-ethylcarbodiimide hydrochloride (EDC.HCl) (0.12 g) and 4-dimethylaminopyridine (DMAP) (0.051 g) is dissolved in dry dichloromethane (ca. 3 mL) under nitrogen. A solution of 6-(4-isopropoxyphenyl)-6-(4-(3-hydroxy-1-propoxy)phenyl)-3-methoxy-9,10-dihydro-6H-benzo[h]naphtho[2,1-f]chromene (0.25 g, prepared using methods referred to and described in US Patent Application 2010/0056810 A1, and modified methods thereof which are known to those skilled in the art) in dry dichloromethane (ca. 2-3 mL) is then added via syringe and the mixture stirred at ambient temperature for 2 hours. The solvent is evaporated in vacuo and the residue purified by column chromatography using silica gel, giving the product conjugate (telechelic) bis(naphthopyran succinate) end-functionalised poly(propylene oxide).

3,3-Di(4-methoxyphenyl)-13-(2-hydroxyethoxy)-13-methyl-indeno[2,1-f]naphtho[1,2-b]pyran (0.10 g, see Example 1, Step 2) was dissolved in dry dichloromethane (ca. 5 mL) under nitrogen, to which was added triethylamine (0.05 mL) followed by propionyl chloride (0.019 mL) via syringe. The mixture was stirred at ambient temperature for 20 minutes after which the solvent was evaporated in vacuo and the residue purified by column chromatography (silica gel, diethyl ether/hexane, 1:1), giving the product as a purple solid (0.087 g). The structure and purity was confirmed by $^1$H NMR analysis.

Comparative Example 2

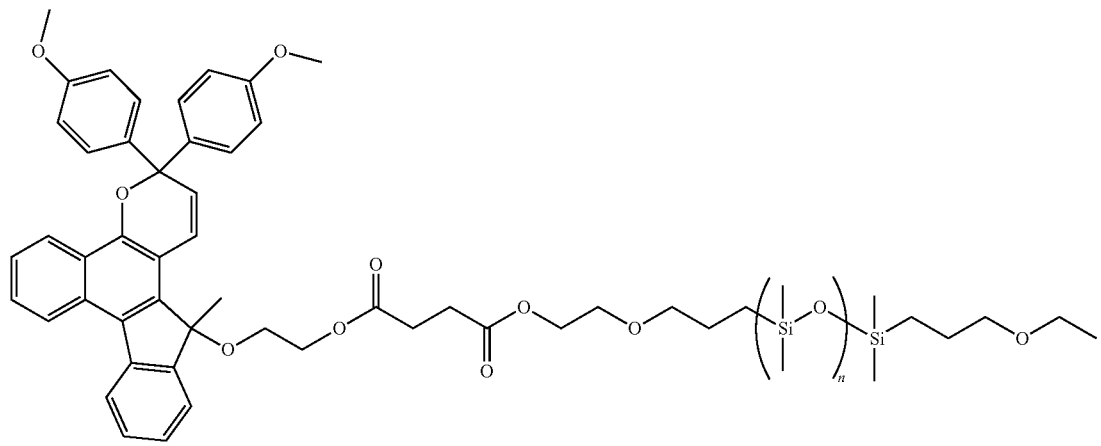

This conjugate was synthesised according to the procedures outlined in Evans et al. WO 2009/146509 A1 and Malic et al. *Macromolecules,* 2010, 43, 8488, using the photochromic dye 3,3-di(4-methoxyphenyl)-13-(2-hydroxyethoxy)-13-methyl-indeno[2,1-f]naphtho[1,2-b]pyran (see Example 1, Step 2) and bis-hydroxyl end-functionalised poly(dimethylsiloxane), (Gelest Inc., PDMS product code DMS-C15). Analysis of this conjugate by $^1$H NMR confirmed the structure and gave a calculated average molecular weight of 2,526 ($n_{PDMS}$=13.3).

Comparative Examples 3 and 4

An amount of the product photochromic conjugate from Comparative Example 2 was taken and fractionated by column chromatography (silica gel, diethyl ether/petroleum ether, 2:1). The conjugate eluted as a broad band of which 3 fractions were collected. The front-running and tail-end fractions were analysed by $^1$H NMR ($d_6$-acetone) to determine their average molecular weights, and were calculated to be 3,196 ($n_{PDMS}$=22.3) and 2,076 ($n_{PDMS}$=7.2), which are herein designated as Comparative Example 3 and Comparative Example 4, respectively. The middle fraction was not analysed. Comparative Examples 3 and 4 were then incorporated into the test lens matrix as described in the section below.

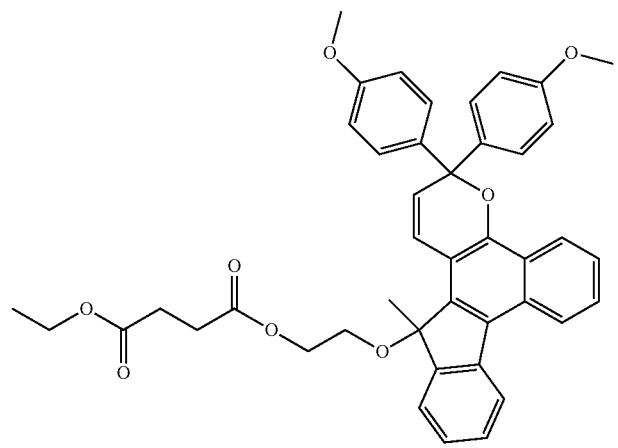

Comparative Example 5

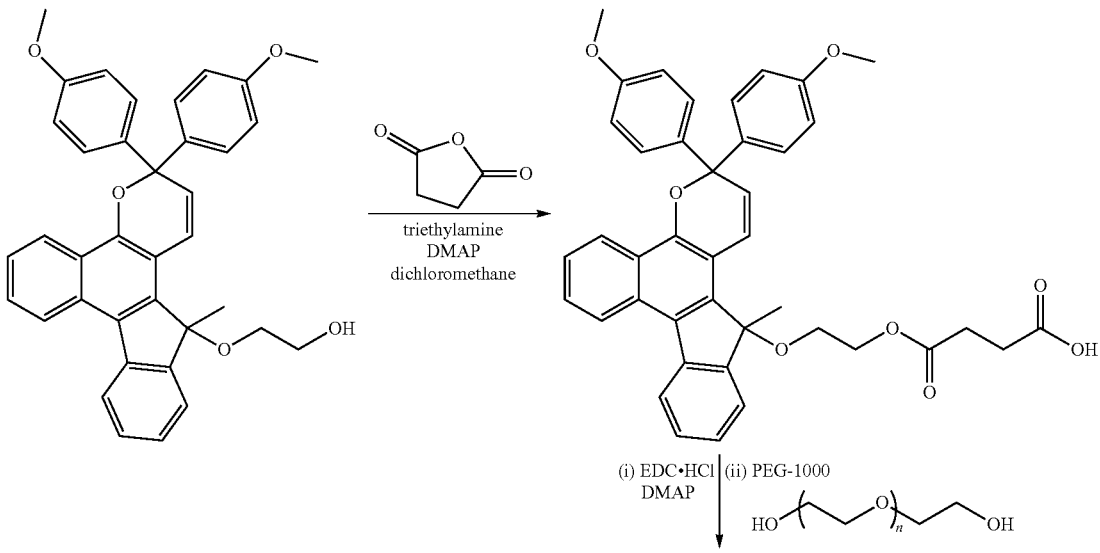

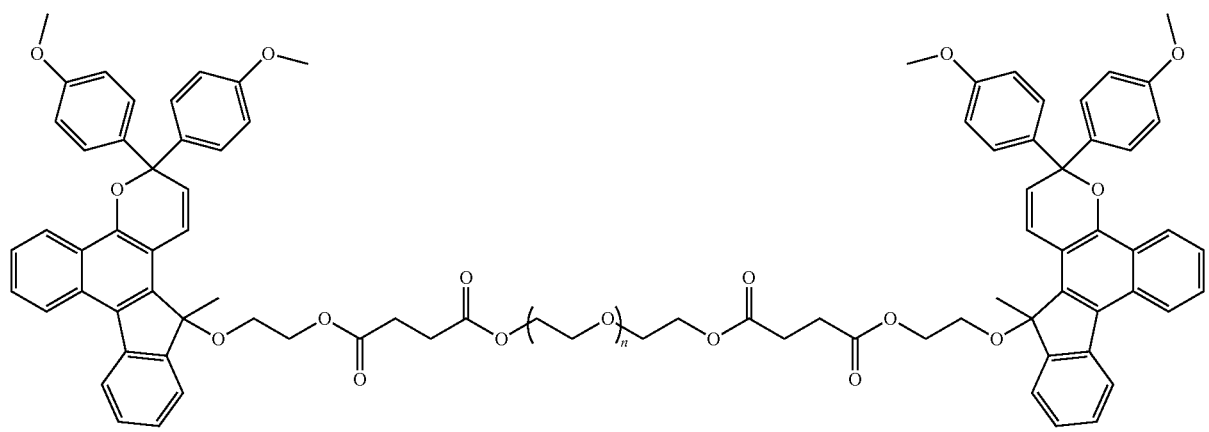

3,3-Di(4-methoxyphenyl)-13-(2-hydroxyethoxy)-13-methyl-indeno[2,1-f]naphtho[1,2-b]pyran (see Example 1, Step 2), succinic anhydride (1 molar equivalent), triethylamine (1.5 molar equivalents) and 4-dimethylaminopyridine (0.1 molar equivalents) were combined in dry dichloromethane under nitrogen and stirred at ambient temperature for 1 hour. To this solution was added N-(3-dimethylaminopropyl)-N'-ethylcarbodiimide hydrochloride (EDC.HCl, 1.5 molar equivalents) followed by poly(ethylene oxide) (PEO, average molecular weight=1,000, 0.5 molar equivalents). The mixture was stirred for a further 1 hour and the product isolated by column chromatography (silica gel, dichloromethane/5-10% MeOH). The product was analysed by $^1$H NMR, which confirmed its purity and gave a calculated average molecular weight of 2,088 ($n_{PEO}$=17.0) based upon integrations of selected resonance peaks of the photochromic moieties and the conjugated polymer.

Comparative Example 6

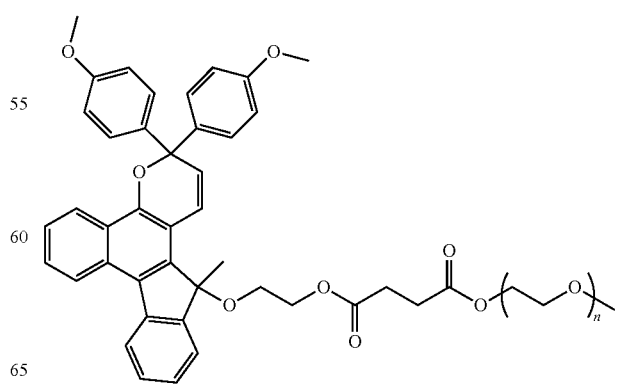

This conjugate was synthesised according to the procedures outlined in patent WO 2004/041961 A1, using succinic acid chloride mono-PEG(750) ester and the hydroxyl-functionalised photochromic dye 3,3-Di(4-methoxyphenyl)-13-(2-hydroxyethoxy)-13-methyl-indeno[2,1-f]naphtho[1,2-b]pyran (see Example 1, Step 2).

Photochromic Testing Procedure

Photochromic conjugates outlined in the examples herein and their corresponding comparative examples (controls) were incorporated within a standard thermoset lens matrix formulation composed of 4 parts (by weight) ethoxylated Bisphenol A dimethacrylate (EBPDMA, EO/phenol=1.3), 1 part poly(ethylene glycol) 400 dimethacrylate (PEGDMA) and 0.4 wt % AIBN (radical initiator), at an effective dye concentration of $1.5\times10^{-7}$ mol/g. The mixtures were added to a mold and thermally cured in a temperature programmable oven set to raise the temperature from 40° C. to 95° C. at a rate of 12° C./hour and then maintained at 95° C. for 3 hours. The test lenses produced had a thickness of 1.67 mm and were subjected to kinetic testing using a light table comprising a UV-vis spectrophotometer and an external UV light source. The samples were irradiated with filtered UV light (365 nm) for a duration of 900 seconds (15 minutes, coloration) at which point the light source was turned off and the sample was further monitored in the dark (decoloration) for a minimum of 30 minutes. The temperature of the lens samples was maintained at 23° C. in a water bath using a Peltier temperature controller. The resulting change in absorbance during coloration and decoloration was monitored over time at $\lambda_{max}$ (maximum wavelength of absorption of the coloured form of the photochromic compound). Fade speeds of all photochromic compounds herein are expressed as values of $t_{1/2}$ and $t_{3/4}$ which are defined as the time taken for the initial absorbance value (after 15 minutes UV irradiation) to be reduced by half and three quarters, respectively.

TABLE 1

Fade-speeds (decolouration) of compounds of the invention and comparative (control) examples.

| Examples | $t_{1/2}$ (sec) | $t_{3/4}$ (sec) |
|---|---|---|
| 1 ($n_{PPO}$ = 36.3) | 37 | 88 |
| 2 ($n_{PPO}$ = 18.4) | 42 | 109 |
| 3 (glycerol propoxylate, $n_{PPO}$ = 25.2) | 39 | 99 |
| 4 ($n_{PBO}$ = 16.7) | 42 | 108 |
| 5 ($n_{PBO}$ = 13.1) | 45 | 122 |
| CE 1 (propionate control) | 88 | 366 |
| CE 2 ($n_{PDMS}$ = 13.3) | 40 | 100 |
| CE 3 ($n_{PDMS}$ = 22.3) | 35 | 85 |
| CE 4 ($n_{PDMS}$ = 7.2) | 45 | 124 |
| CE 5 ($n_{PEO}$ = 17.0) | 51 | 152 |
| CE 6 (mono-end functional, $n_{PEO}$ = 16.2) | 57 | 182 |

$\lambda_{max}$ = 560 nm.

Examples 10A to 25C

Photochromic polymer compounds of Examples 6A to 21C shown in Table 3 may be prepared in an analogous manner to the photochromic polymers of Examples 1 and 2 from the polymer precursor structures A, B or C (as identified in the column headed "Pre") of structures shown in Table 2 by reaction of this polymer precursor with the photochromic identified in Table 3 (each numerical example examines a specific photochromic and the polymer adducts with prepolymer A, B and C.

TABLE 2

Structure of polymer precursor

| Polymer Precursor | Structure |
|---|---|
| A (see Example 1 Step 1) | 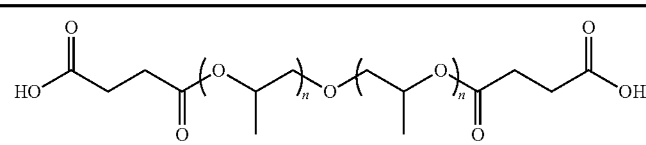 |
| B (see Examples 4 & 5 step 1) | 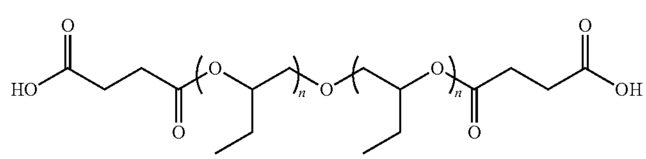 |
| C (see Example 2 Step 1) | 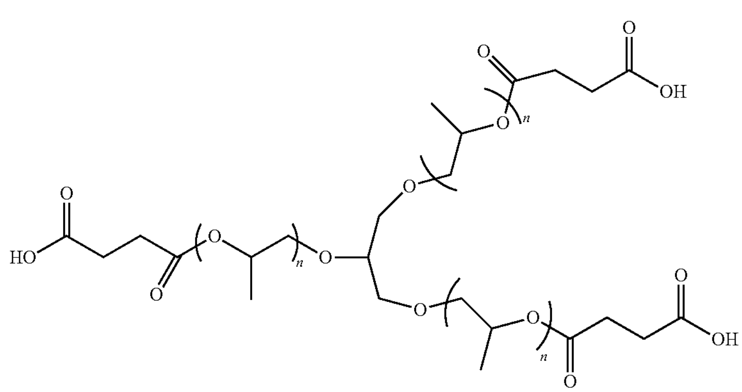 |

TABLE 3
Polymer precursor, photochromic and structure of resultant photochromic polymer
| Ex | Pre | Photochromic | Photochromic Polymer |
|----|-----|--------------|----------------------|
| 10 | A | 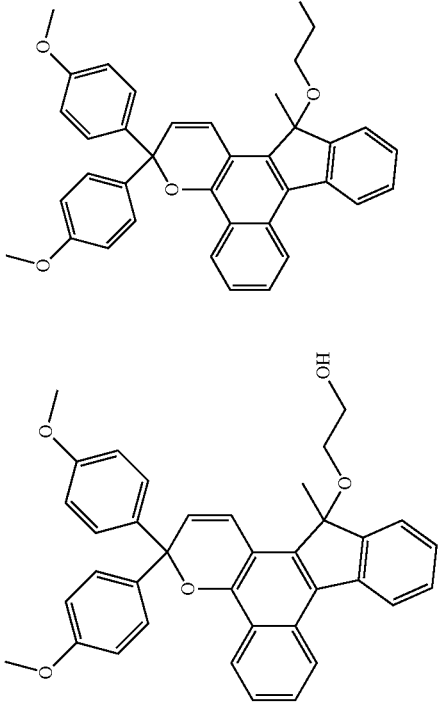 | 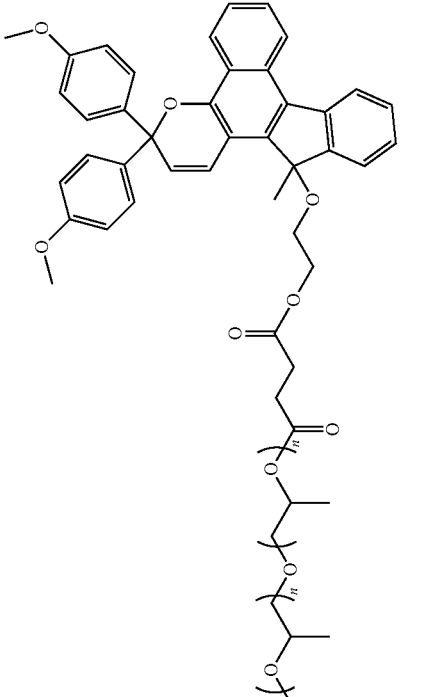 |
| 10 | B |  | 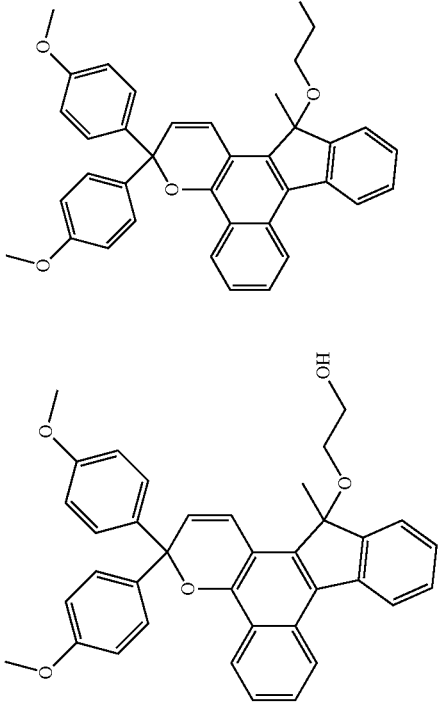 |

TABLE 3-continued
Polymer precursor, photochromic and structure of resultant photochromic polymer
| Ex | Pre | Photochromic | Photochromic Polymer |
|---|---|---|---|
| 10 | C | | 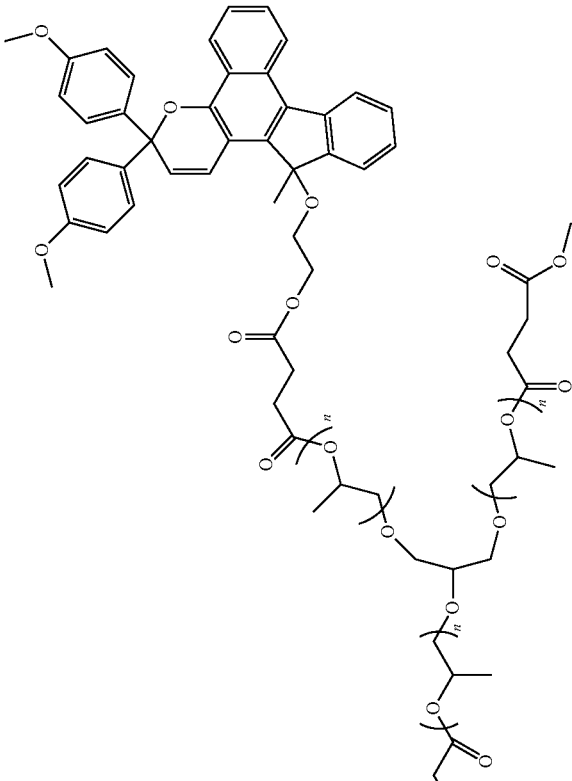 |

TABLE 3-continued

Polymer precursor, photochromic and structure of resultant photochromic polymer

| Ex | Pre | Photochromic | Photochromic Polymer |
|----|-----|--------------|----------------------|
| 11 | A | | |
| 11 | B | | |

TABLE 3-continued
Polymer precursor, photochromic and structure of resultant photochromic polymer
| Ex | Pre | Photochromic | Photochromic Polymer |
|----|-----|--------------|----------------------|
| 11 | C | | 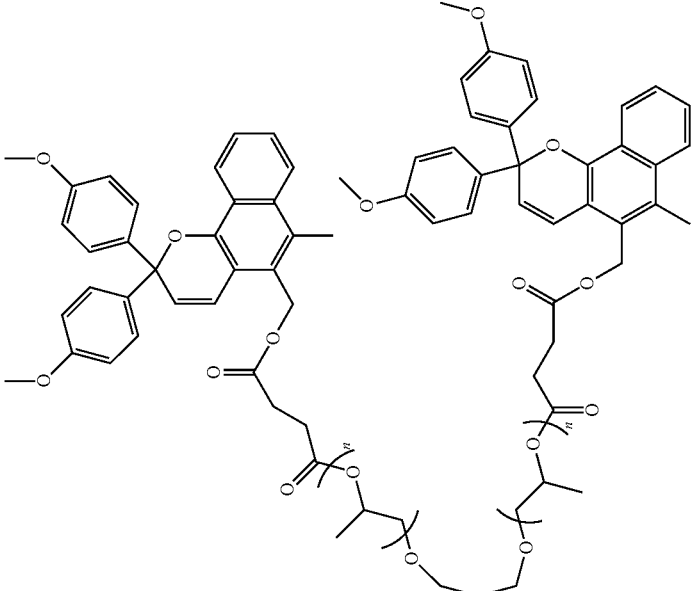 |

TABLE 3-continued
Polymer precursor, photochromic and structure of resultant photochromic polymer
| Ex | Pre | Photochromic | Photochromic Polymer |
|---|---|---|---|
| 12 | A | 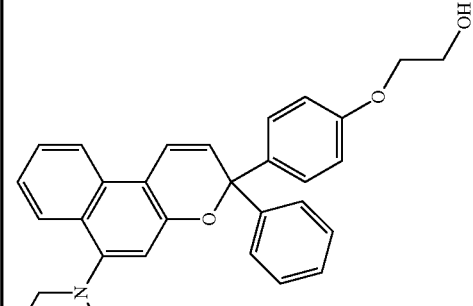 | 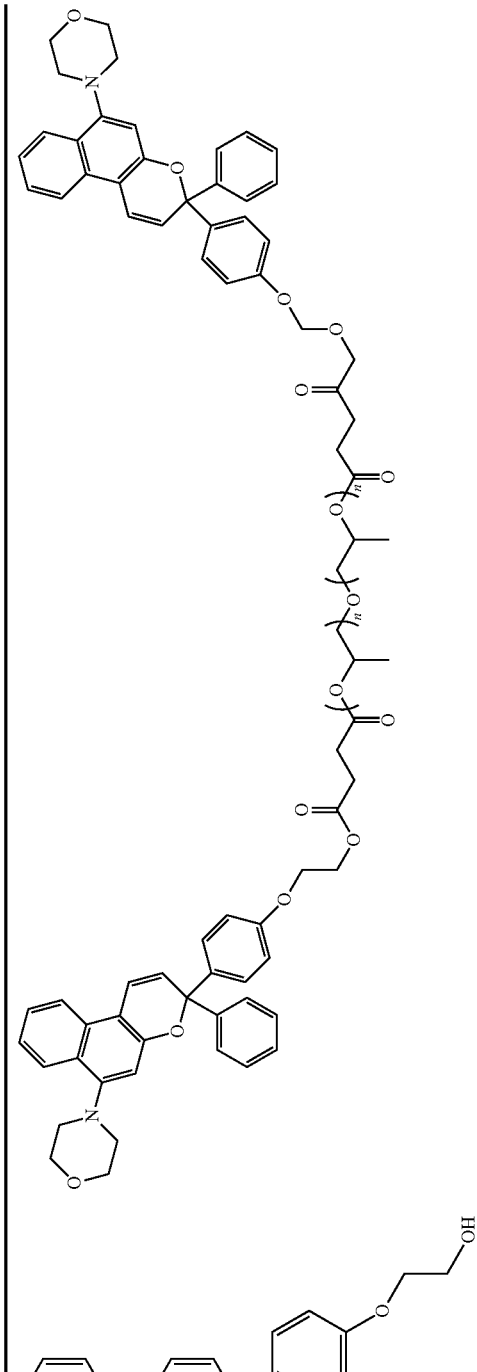 |
| 12 | B | | 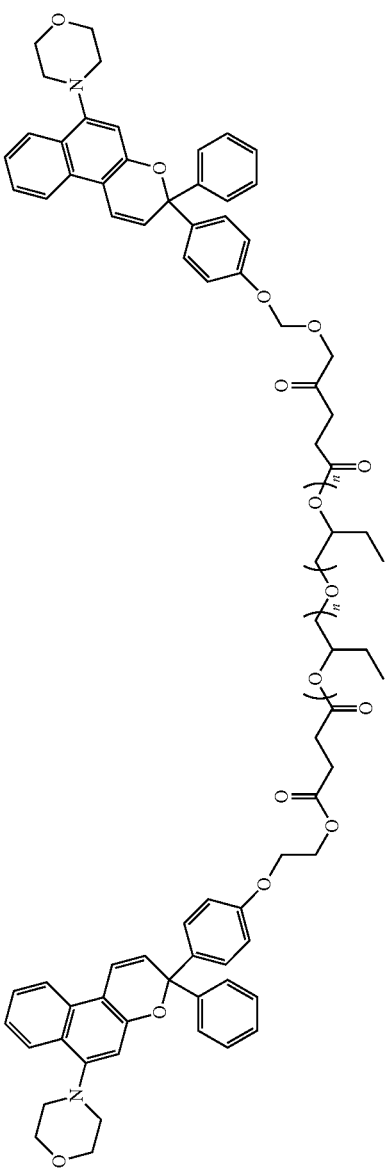 |

TABLE 3-continued

Polymer precursor, photochromic and structure of resultant photochromic polymer

| Ex | Pre | Photochromic | Photochromic Polymer |
|----|-----|--------------|----------------------|
| 12 | C | | |
| 13 | A | | |

TABLE 3-continued
Polymer precursor, photochromic and structure of resultant photochromic polymer
| Ex | Pre | Photochromic | Photochromic Polymer |
|---|---|---|---|
| 13 | B | | 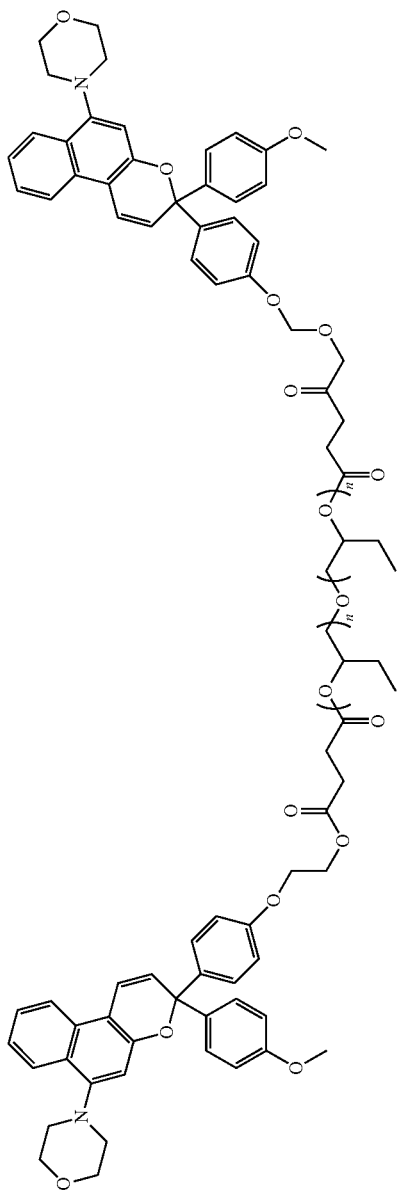 |
| 13 | C | | 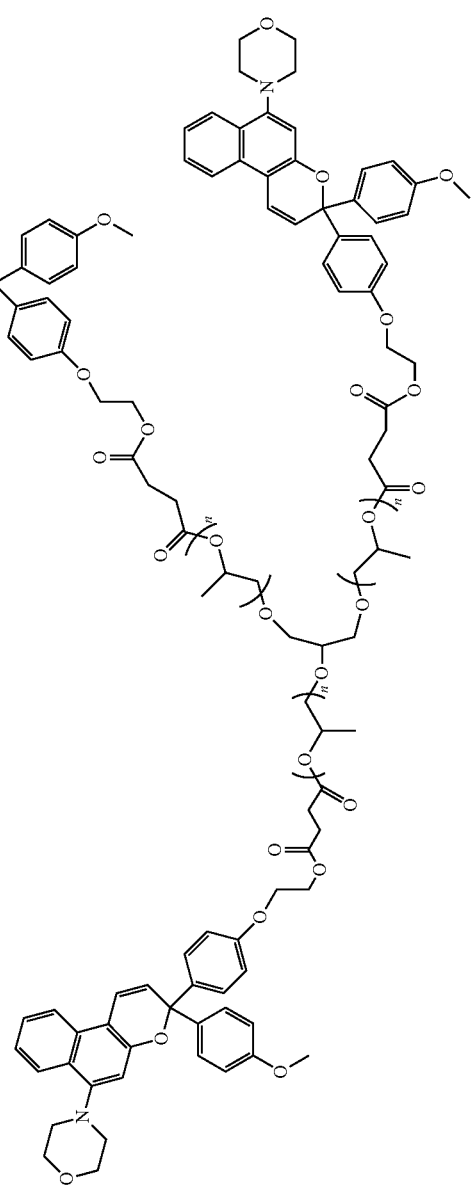 |

TABLE 3-continued
Polymer precursor, photochromic and structure of resultant photochromic polymer
| Ex | Pre | Photochromic | Photochromic Polymer |
|---|---|---|---|
| 14 | A | 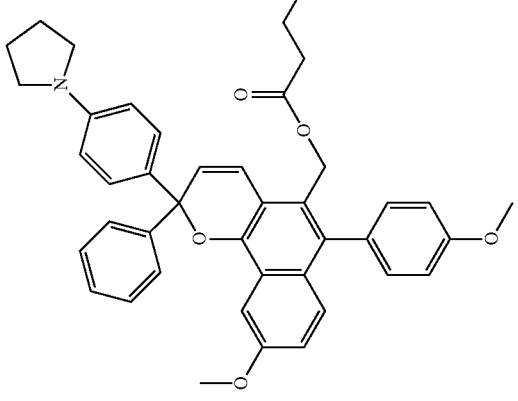 | 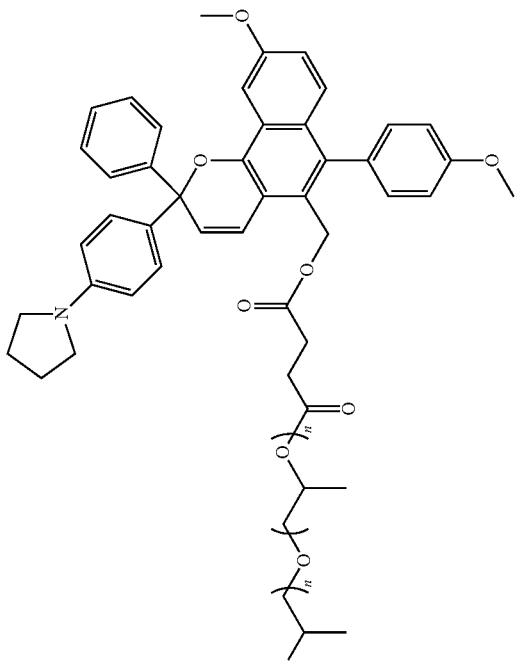 |

TABLE 3-continued

Polymer precursor, photochromic and structure of resultant photochromic polymer

| Ex | Pre | Photochromic | Photochromic Polymer |
|----|-----|--------------|----------------------|
| 14 | B   |              |                      |

TABLE 3-continued
Polymer precursor, photochromic and structure of resultant photochromic polymer
| Ex | Pre | Photochromic | Photochromic Polymer |
|---|---|---|---|
| 14 | C | | 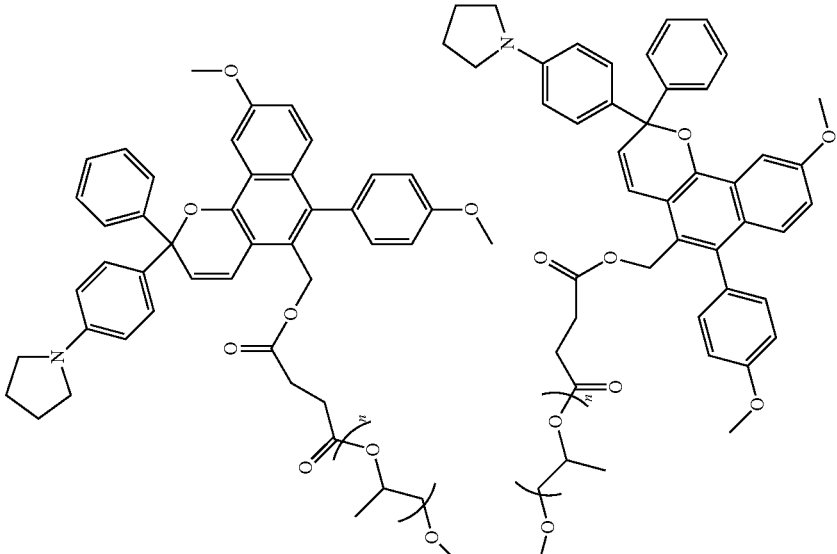 |

TABLE 3-continued

Polymer precursor, photochromic and structure of resultant photochromic polymer

| Ex | Pre | Photochromic | Photochromic Polymer |
|---|---|---|---|
| 15 | A | | |
| 15 | B | | |
| 15 | C | | |

TABLE 3-continued
Polymer precursor, photochromic and structure of resultant photochromic polymer
| Ex | Pre | Photochromic | Photochromic Polymer |
|---|---|---|---|
| 16 | A | 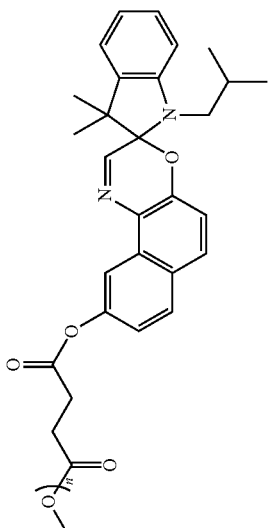 | 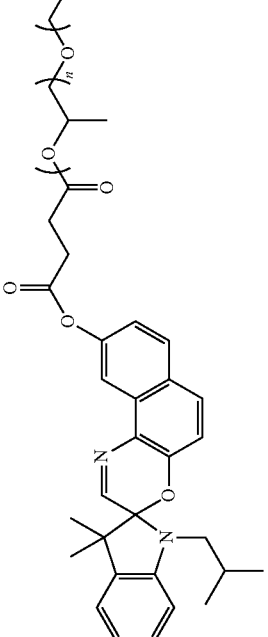 |
| 16 | B | | 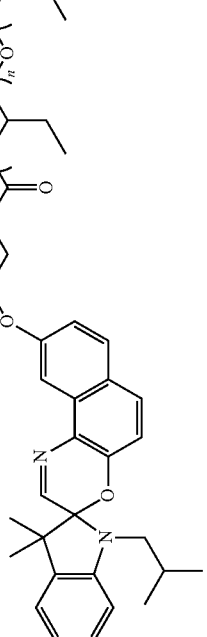 |

TABLE 3-continued

Polymer precursor, photochromic and structure of resultant photochromic polymer

| Ex | Pre | Photochromic | Photochromic Polymer |
|---|---|---|---|
| 16 | C | | |
| 17 | A | | |

TABLE 3-continued
Polymer precursor, photochromic and structure of resultant photochromic polymer
| Ex | Pre | Photochromic | Photochromic Polymer |
|----|-----|--------------|----------------------|
| 17 | B | 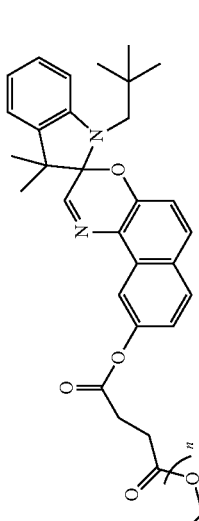 | |
| 17 | C | | 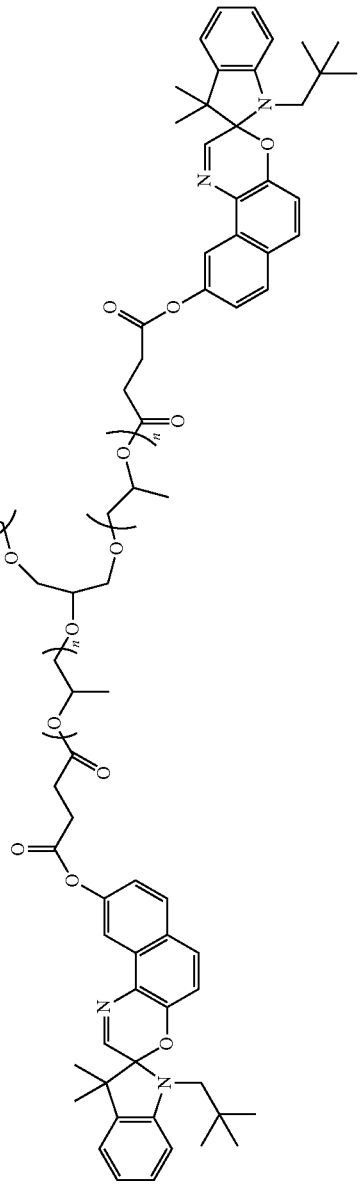 |

TABLE 3-continued

Polymer precursor, photochromic and structure of resultant photochromic polymer

| Ex | Pre | Photochromic | Photochromic Polymer |
|---|---|---|---|
| 18 | A | | |
| 18 | B | | |

TABLE 3-continued

Polymer precursor, photochromic and structure of resultant photochromic polymer

| Ex | Pre | Photochromic | Photochromic Polymer |
|---|---|---|---|
| 18 | C | | |
| 19 | A | | |

TABLE 3-continued
Polymer precursor, photochromic and structure of resultant photochromic polymer
| Ex | Pre | Photochromic | Photochromic Polymer |
|---|---|---|---|
| 19 | B | | 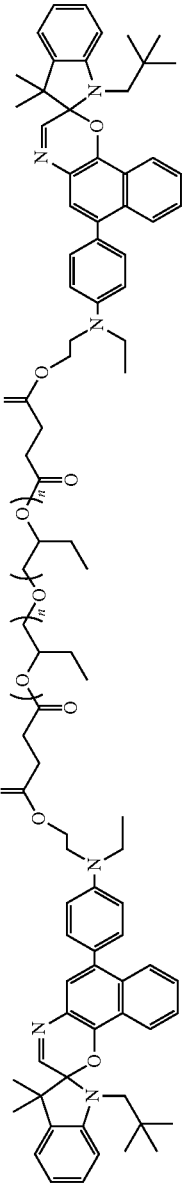 |
| 19 | C | | 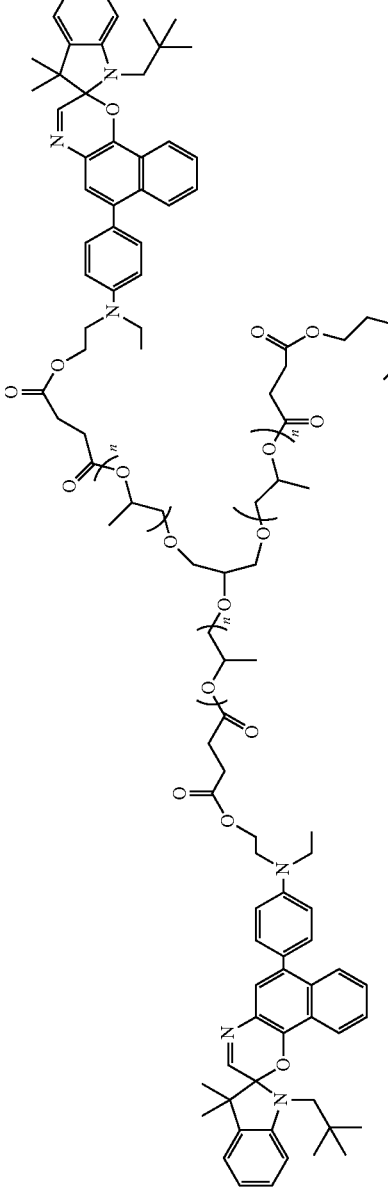 |

TABLE 3-continued

Polymer precursor, photochromic and structure of resultant photochromic polymer

| Ex | Pre | Photochromic | Photochromic Polymer |
|---|---|---|---|
| 20 | A | | |
| 20 | B | | |

TABLE 3-continued
Polymer precursor, photochromic and structure of resultant photochromic polymer
| Ex | Pre | Photochromic | Photochromic Polymer |
|---|---|---|---|
| 20 | C | | 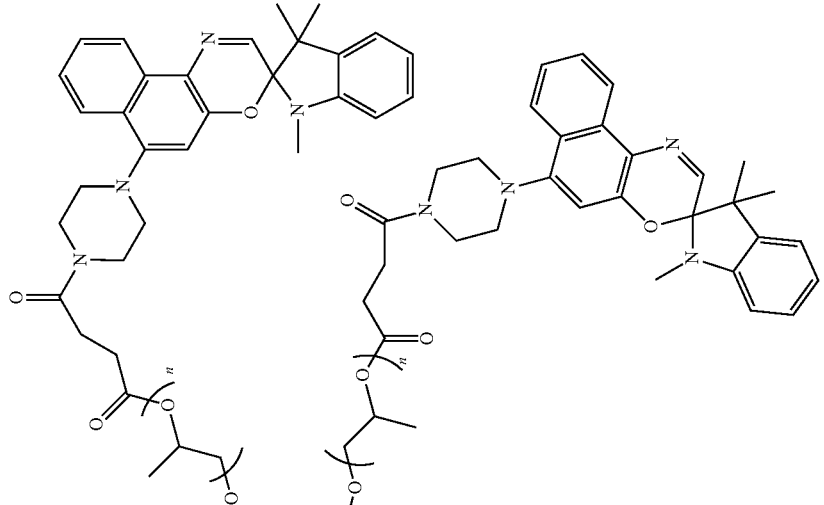 |

TABLE 3-continued
Polymer precursor, photochromic and structure of resultant photochromic polymer
| Ex | Pre | Photochromic | Photochromic Polymer |
|---|---|---|---|
| 21 | A |  |  |
| 21 | B | | 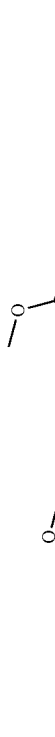 |

TABLE 3-continued

Polymer precursor, photochromic and structure of resultant photochromic polymer

| Ex | Pre | Photochromic | Photochromic Polymer |
|---|---|---|---|
| 21 | C | | |

TABLE 3-continued

Polymer precursor, photochromic and structure of resultant photochromic polymer

| Ex | Pre | Photochromic | Photochromic Polymer |
|----|-----|--------------|----------------------|
| 22 | A   |              |                      |
| 22 | B   |              |                      |

TABLE 3-continued
Polymer precursor, photochromic and structure of resultant photochromic polymer
| Ex | Pre | Photochromic | Photochromic Polymer |
|---|---|---|---|
| 22 | C | | 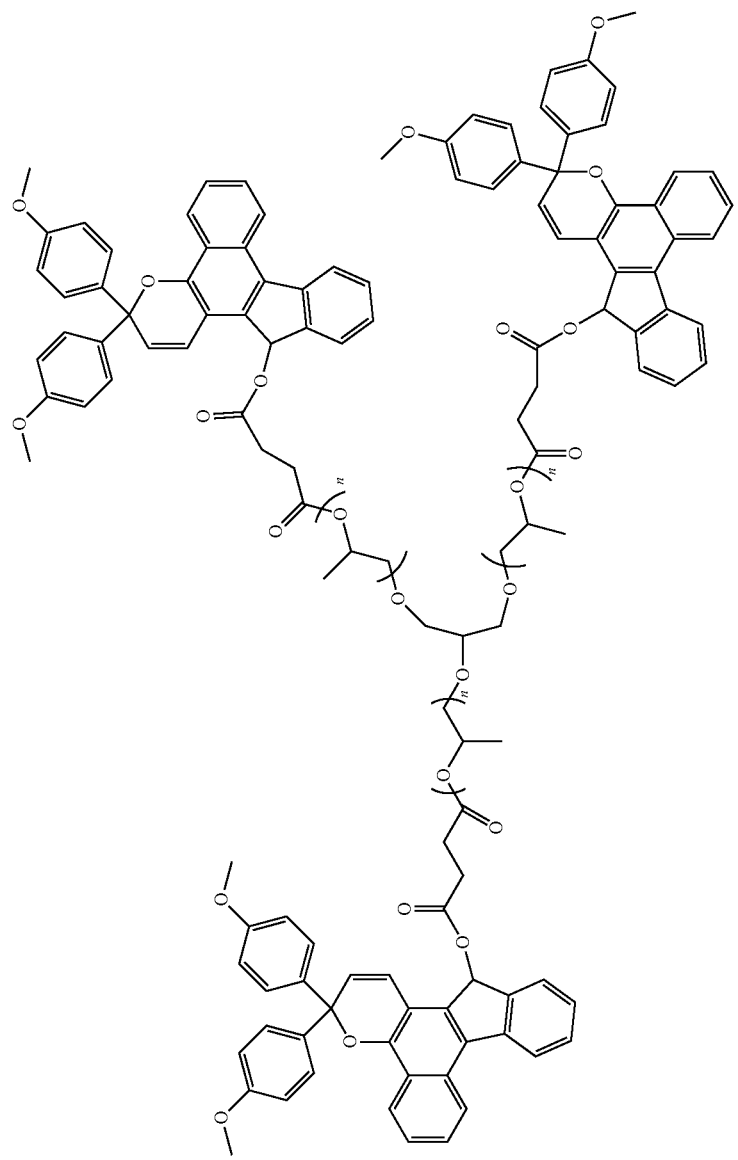 |

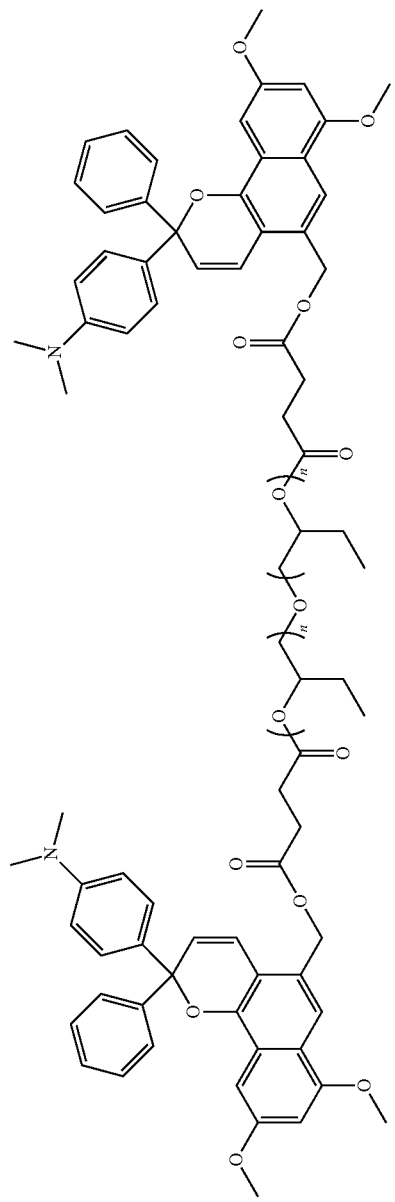

TABLE 3-continued

Polymer precursor, photochromic and structure of resultant photochromic polymer

| Ex | Pre | Photochromic | Photochromic Polymer |
|---|---|---|---|
| 23 | C | | |

TABLE 3-continued
Polymer precursor, photochromic and structure of resultant photochromic polymer
| Ex | Pre | Photochromic | Photochromic Polymer |
|---|---|---|---|
| 24 | A | 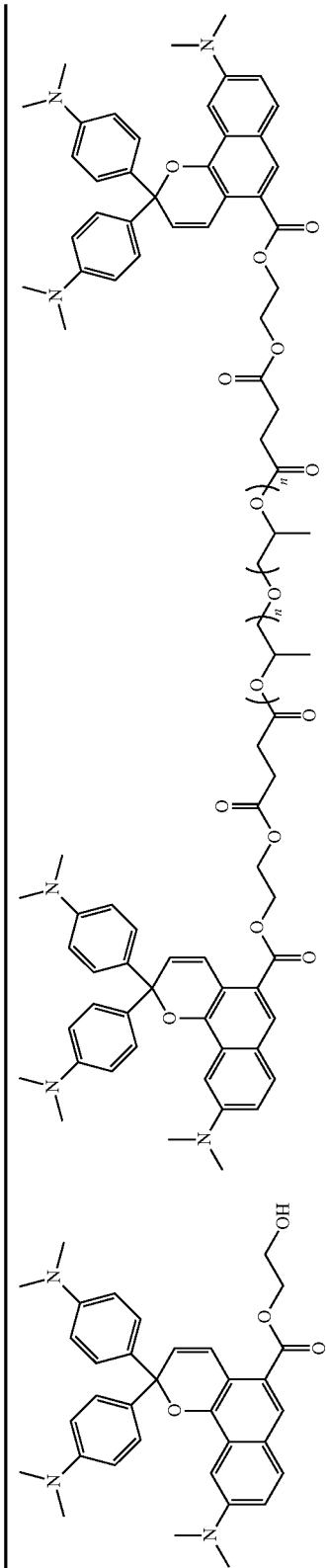 | 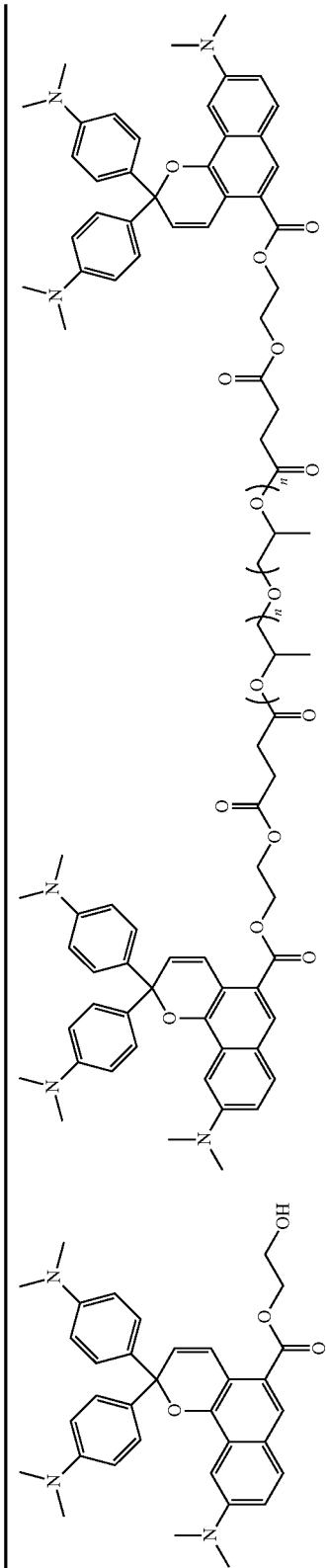 |
| 24 | B | | 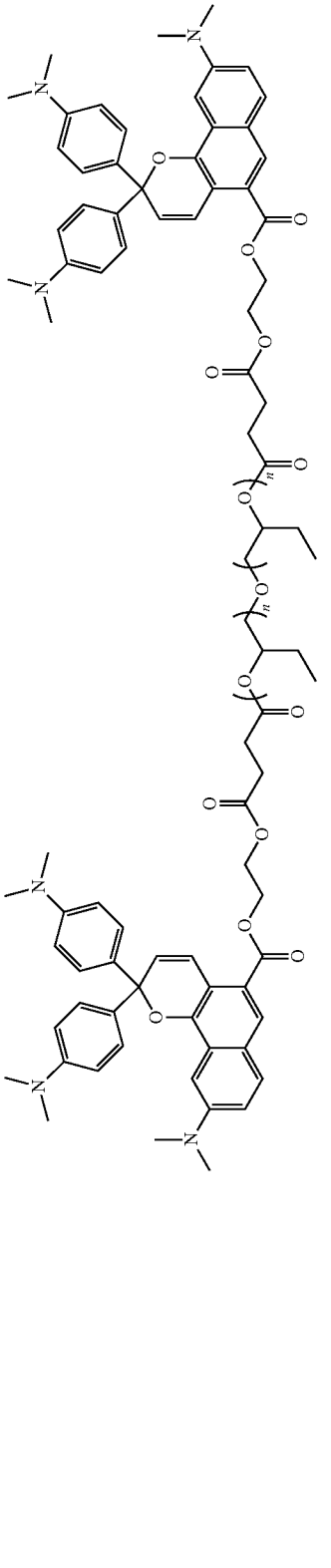 |

TABLE 3-continued

Polymer precursor, photochromic and structure of resultant photochromic polymer

| Ex | Pre | Photochromic | Photochromic Polymer |
|---|---|---|---|
| 24 | C | | |

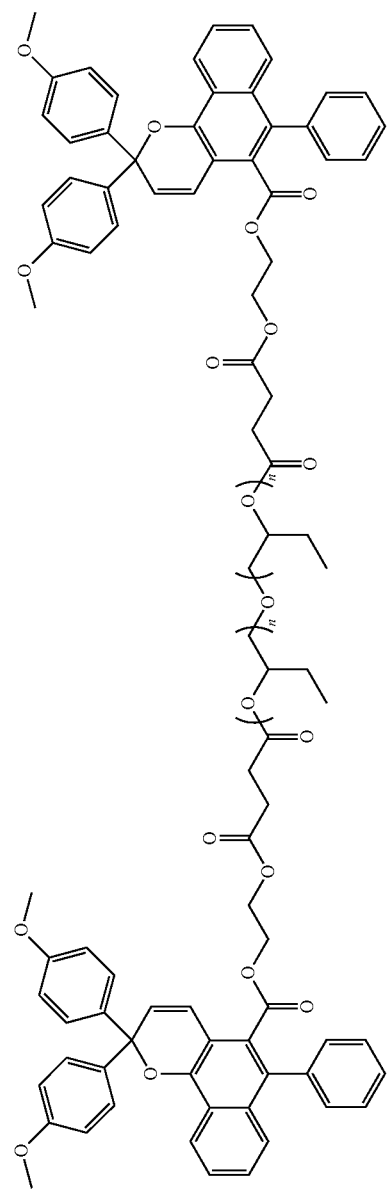

TABLE 3-continued
Polymer precursor, photochromic and structure of resultant photochromic polymer
| Ex | Pre | Photochromic | Photochromic Polymer |
|----|-----|--------------|----------------------|
| 25 | C | | 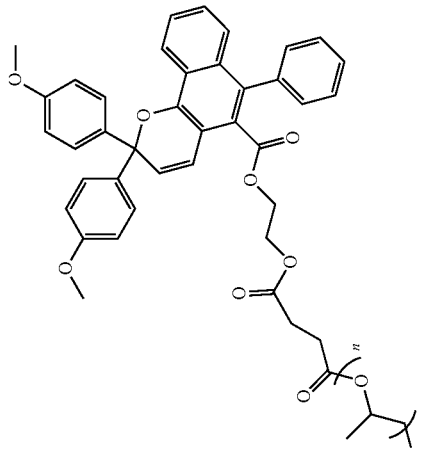 |

The invention claimed is:

1. A photochromic polymer of formula I:

(PC-L-(RO)$_n$—)$_z$X    I wherein:
Z is from 2 to 8;
PC are independently selected photochromic moieties;
L are independently selected from a bond and linkers;
R are independently selected polymer chains selected from the group consisting of $C_2$ to $C_4$ alkylene and $C_1$ to $C_{10}$ alkoxy substituted ($C_2$ to $C_4$ alkylene);
n is an integer from 1 to 50;
X is a hydrocarbon comprising from 1 to 20 carbon atoms or a hydrocarbon ether or polyether of 2, 3 or 4 hydrocarbon units each of 3 to 6 carbon atoms joined through ether linkages and together providing covalent bonds to from 2 to 8 (PC-L-(RO)$_n$—) units; and
wherein the photochromic polymer does not comprise silicon.

2. A photochromic polymer according to claim 1 wherein X is a hydrocarbon of formula:

$C_mH_{2m+2-z}$ wherein m is from 1 to 6 and Z is as defined in claim 1.

3. A photochromic polymer according to claim 1 wherein X is selected from the group consisting of ethyl, propyl, butyl, pentyl, and hexyl wherein z is 2; or
X is selected from the group consisting of

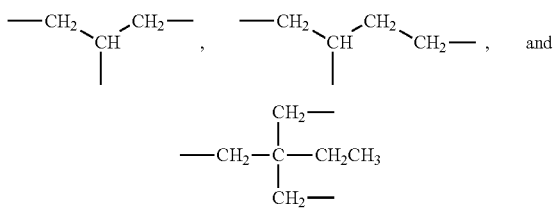

wherein z is 3; or
X is selected from the group consisting of

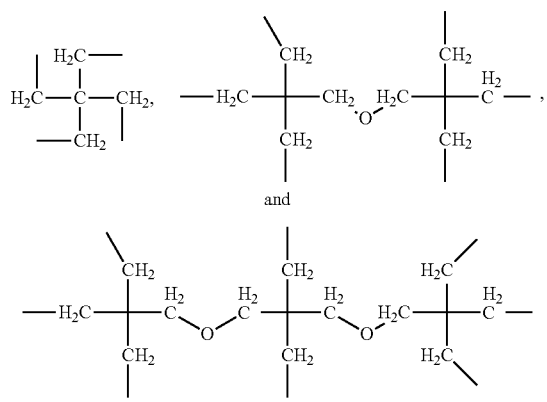

wherein z is 4, 6 or 8.

4. A photochromic polymer according to claim 1 comprising a poly(alkylene oxide) polymer which is selected from poly(propylene oxide) and copolymers comprising propylene oxide and one or more of ethylene oxide and butylene oxide.

5. A photochromic polymer according to claim 1, wherein (RO)$_n$ is selected from poly(propylene oxide), polybutylene oxide, block copolymers of poly(propylene oxide) and poly(butylene oxide), block copolymers of poly(ethylene oxide) and poly(propylene oxide), block copolymers of poly(ethylene oxide) and poly(butylene oxide) and block copolymers of poly(ethylene oxide), poly(propylene oxide) and poly(butylene oxide) wherein the total of the poly(propylene oxide) and poly(butylene oxide) blocks provides a molecular weight in the range of from 200 to 10,000.

6. A photochromic polymer of claim 1 wherein the photochromic polymer is of formula IIa, IIb or IIc:

PC$^1$-L$^1$-(R$^a$O)$_{n1}$—X$^1$—(OR$^b$)$_{n2}$-L$^2$-PC$^2$    IIa wherein X$^1$ is selected from the group consisting of ethyl, propyl, butyl, pentyl and hexyl;

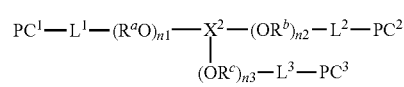

wherein X$^2$ is of formula $C_mH_{2m-1}$ (straight or branched chain) wherein m is from 1 to 6;

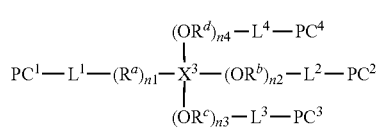

wherein X$^3$ is of formula $C_mH_{2m-2}$ (straight or branched chain) wherein m is from 1 to 6;
PC$^1$, PC$^2$, PC$^3$ and PC$^4$ are defined as for PC;
L$^1$, L$^2$, L$^3$ and L$^4$ are as defined for L;
R$^a$, R$^b$, R$^c$ and R$^d$ are as defined for R;
and
n1, n2, n3 and n4 are from 1 to 20.

7. A photochromic polymer according to claim 6 of formula IIa wherein R$^a$ and R$^b$ are polypropylene and X is propylene.

8. A photochromic polymer according to claim 1 wherein L are selected from the group consisting of:
a bond;

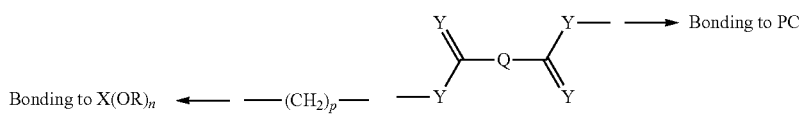

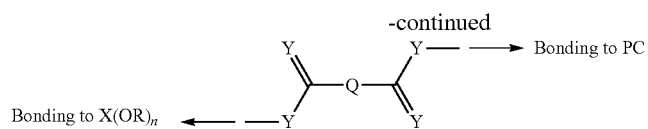

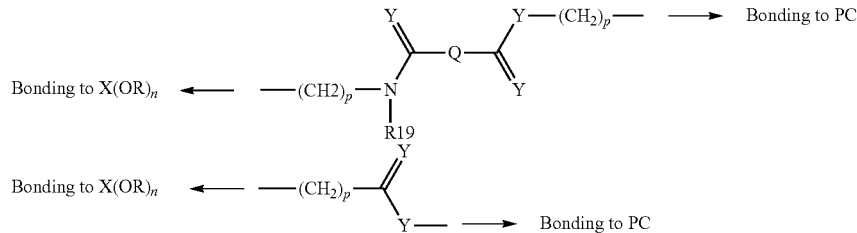

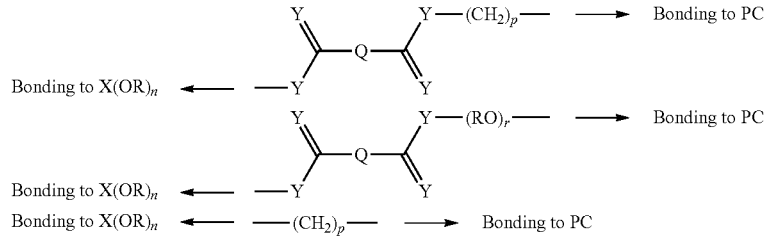

wherein
- Y is independently NR19, oxygen or sulphur,
- R19 is hydrogen or $C_{1-10}$ alkyl,
- p is an integer from 1 to 15,
- r is an integer from 0 to 10, and
- Q is $C_{1-10}$ alkyl, $C_{1-10}$ alkenyl or aryl optionally further substituted by $C_1$ to $C_{10}$ alkyl, or substituted heteroaryl.

9. A photochromic polymer according to claim 1 wherein the photochromic moieties are independently selected from the group consisting of naphthopyrans, spiropyrans and spirooxazines.

10. A photochromic polymer according to claim 1 wherein the photochromic moieties are independently selected from the moieties of formula IIIa to IIId:

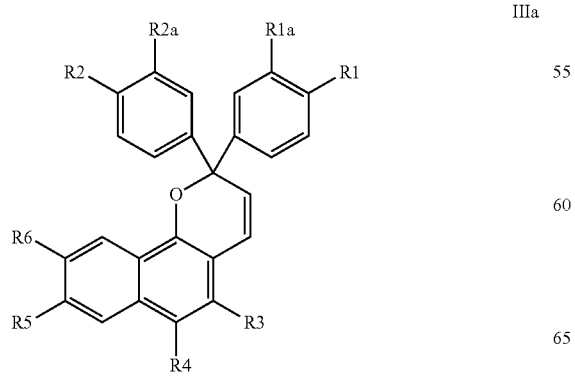

IIIa

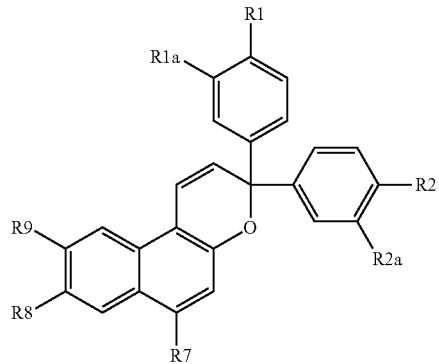

IIIb

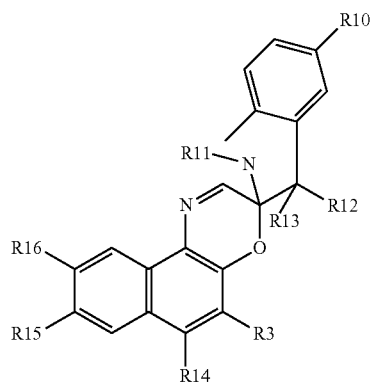

IIIc

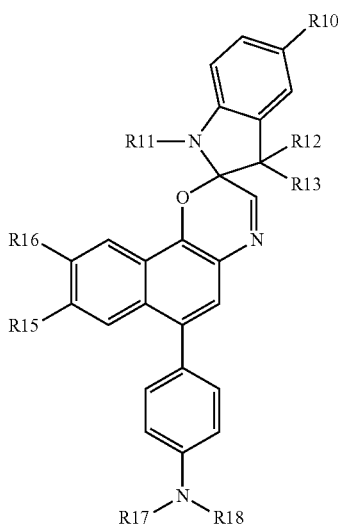

IIId wherein R1 and R2 independently represent hydrogen, $C_{1-10}$ alkyl, $C_{1-10}$ alkoxy, $C_{1-10}$ hydroxyalkoxy, $C_{1-10}$ alkoxy($C_{1-10}$) alkoxy, phenyl, $C_{1-10}$ alkoxyphenyl, halogen $C_{1-5}$ haloalkyl, $C_{1-5}$ alkylamino, $C_{1-5}$ dialkylamino, arylamino, diarylamino, aryl $C_{1-5}$ alkylamino, or a cyclic amino group;

R1a and R2a are hydrogen or together with R1 and R2 respectively may form a carbocyclic or heterocyclic ring of 5 or 6 constituent ring members and optionally up to two heteroatoms selected from oxygen, sulfur and —N(R19)- wherein R19 is selected from hydrogen and $C_{1-10}$ alkyl;

R3 represents hydrogen, $C_{1-10}$ alkyl, up to $C_{20}$ cycloalkyl, up to $C_{20}$ bicycloalkyl, $C_{2-10}$ alkenyl, $C_{1-10}$ alkoxy, $C_{1-10}$ hydroxyalkyl, $C_{1-10}$ alkoxy ($C_{1-10}$) alkyl, $C_{1-10}$ aminoalkyl, $C_{1-20}$ alkoxycarbonyl, carboxyl, halogen, aryloxycarbonyl, formyl, acetyl or aroyl;

R4 represents, phenyl, $C_{1-10}$ alkoxyphenyl, $C_{1-10}$ dialkoxyphenyl, $C_{1-10}$ alkylphenyl, $C_{1-10}$ dialkylphenyl or one of the groups specified for R3;

or R3 and R4 together form a cyclic structure of the type

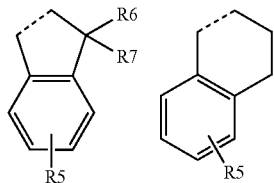

R5, R6, R7, R8, R9, R10, R14, R15, R16 are as defined for R1 and R2; and

R11 represents a linear or branched $C_{1-10}$ alkyl, $C_{1-10}$ hydroxyalkyl, or a $C_{5-7}$ ring.

11. A photochromic polymer of formula I according to claim 1 wherein the photochromic moieties (PC) are independently selected from the group consisting of (a) 1,3-dihydro-3,3-dimethyl-1-neopentyl-6'-(4'''-N-ethyl, N-(hydroxylethyl)anilino)spiro[2H-indole-2,3'-3H-naphtho[1,2-b][1,4]oxazine;

(b) 3-(4'-methoxyphenyl),3-(4''-(hydroxyethoxy)phenyl)-6-morpholino-3H-naphtho[2,1-b]pyran;

(c) 3-(4'-methoxyphenyl),3-(4''-(hydroxyethoxy)phenyl)-6-morpholino-3H-naphtho[2,1-b]pyran;

(d) 1,3-dihydro-3,3-dimethyl-1-isobutyl-9'-hydroxy-sprio[2H-indole-2,3'-3H-naphtho[2,1-b][1,4]oxazine;

(e) 2-(4'-pyrrolidinophenyl)-2-phenyl-5-hydroxymethyl-6-anisyl-9-methoxy-2H-naphtho[1,2-b]pyran;

(f) 2,2-bis(4'-methoxyphenyl)-5-hydroxymethyl-6-methyl-2H-naphthol[1,2-b]pyran;

(g) (2-(4'-pyrrolidinophenyl)-2-phenyl-5-hydroxymethyl-6-anisyl-9-methoxy-2H-naphtho[1,2-b]pyran;

(h) 3-phenyl-3-(4'-(hydroxyethoxy)phenyl)-6-morpholino-3H-naphtho[2,1-b]pyran;

(i) 1,3-dihydro-3,3-dimethyl-1-neopentyl-9'-hydroxy-spiro[2H-indole-2,3'-3H-naphthol[2,1-b][1,4]oxazine]; and (j) 2,2-Bis(4'-methoxyphenyl)-5-hydroxymethyl-6-methyl-2H-naphtho[1,2-b]pyran.

12. A photochromic polymer according to claim 1 wherein the polymer comprises a poly($C_2$ to $C_4$ alkylene oxide) selected from poly(propylene oxide) and copolymers of propylene oxide with one or both of ethylene oxide and butylene oxide and having a molecular weight in the range of from 200 to 10,000.

13. A photochromic polymer according to claim 1 wherein the glass transition temperature is less than 25° C.

14. A photochromic polymeric composition comprising a photochromic polymer according to claim 1 and a host polymer.

15. A photochromic polymeric composition according to claim 14 which is free from polydialkylsiloxane polymer.

16. A photochromic lens comprising a photochromic polymeric composition according to claim 14.

17. A photochromic polymer according to claim 6, wherein $X^2$ is selected from:

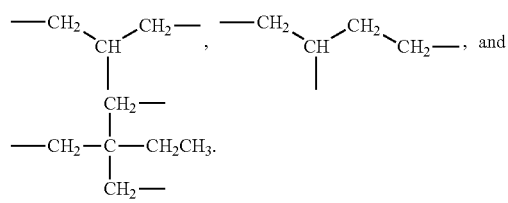

18. A photochromic polymer according to claim 6, wherein $X^3$ is:

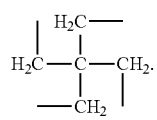

* * * * *